US009340491B2

(12) United States Patent
Menon

(10) Patent No.: US 9,340,491 B2
(45) Date of Patent: *May 17, 2016

(54) NITRILE DERIVATIVES AND THEIR PHARMACEUTICAL USE AND COMPOSITIONS

(71) Applicant: CELLCEUTIX CORPORATION, Beverly, MA (US)

(72) Inventor: Krishna Menon, North Reading, MA (US)

(73) Assignee: Cellceutix Corporation, Beverly, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/685,879

(22) Filed: Nov. 27, 2012

(65) Prior Publication Data

US 2013/0245062 A1    Sep. 19, 2013

Related U.S. Application Data

(63) Continuation of application No. 12/780,132, filed on May 14, 2010, now Pat. No. 8,338,454.

(60) Provisional application No. 61/180,121, filed on May 20, 2009.

(51) Int. Cl.

| *A61K 45/06* | (2006.01) |
|---|---|
| *A61K 31/47* | (2006.01) |
| *A61K 31/44* | (2006.01) |
| *A61K 31/275* | (2006.01) |
| *C07C 255/03* | (2006.01) |
| *A61K 31/277* | (2006.01) |
| *A61K 31/4375* | (2006.01) |
| *A61K 31/472* | (2006.01) |
| *C07C 335/32* | (2006.01) |
| *C07C 335/34* | (2006.01) |
| *C07C 335/36* | (2006.01) |
| *C07D 213/57* | (2006.01) |
| *C07D 215/12* | (2006.01) |
| *C07D 217/02* | (2006.01) |
| *C07D 471/04* | (2006.01) |

(52) U.S. Cl.
CPC ............. *C07C 255/03* (2013.01); *A61K 31/275* (2013.01); *A61K 31/277* (2013.01); *A61K 31/4375* (2013.01); *A61K 31/44* (2013.01); *A61K 31/47* (2013.01); *A61K 31/472* (2013.01); *C07C 335/32* (2013.01); *C07C 335/34* (2013.01); *C07C 335/36* (2013.01); *C07D 213/57* (2013.01); *C07D 215/12* (2013.01); *C07D 217/02* (2013.01); *C07D 471/04* (2013.01); *C07C 2101/02* (2013.01); *C07C 2101/04* (2013.01)

(58) Field of Classification Search
CPC ....... A61K 45/06; A61K 31/47; A61K 31/44; A61K 31/275

USPC .......... 558/426, 433, 438; 514/310, 311, 357, 514/519, 523, 526

See application file for complete search history.

(56) References Cited

U.S. PATENT DOCUMENTS 4,897,105 A    1/1990   Okada et al.
8,338,454 B2 * 12/2012   Menon .......................... 514/307

FOREIGN PATENT DOCUMENTS

| CN | 101550098 A | 7/2009 |
|---|---|---|
| EP | 0 239 064 A2 | 9/1987 |
| GB | 1 202736 | 8/1970 |
| WO | 2007/088545 A2 | 8/2007 |
| WO | 2009/089277 A2 | 7/2009 |

OTHER PUBLICATIONS

Miller et al., JACS, vol. 62, 2099-2103 (1940).
Shapira, et al., Radiation Research, vol. 7, No. 1, 22-34 (1957).
King et al., Biochemistry, vol. 17, No. 8, 1499-1506 (1978).
Southan, et al., Br. J. Pharmacol., vol. 114,510-516 (1995).
Bauer and Welsh, J. Org. Chern. vol. 26, No. 5, 1443-1445 (1961).
Testa et al., Proc. Natl. Acad. Sci ., 2001,98, 10983-10985.
Lawlor et al., J. Cell Sci., 2001,114,2903-2910.
Duan, Circ. Res ., 2000, 86, 15-23.
Gerber et al., Organic Synthesis, vol. 77,186 (2000).
Database Chemcats [Online], Chemical Abstracts Service, Columbus, Ohio, Mar. 10, 2010, Aurora Screen Library: "Order Nr K00.576.680" retrieved from STN Database accession No. 015366800, Order Nr: K00.576.680=CAS Registry Nr: 1173470-63-7; Order Nr: KOO.771.445=CAS Registry Nr: 1215732-92.5; Order Nr: K04.624.156=CAS Registry Nr: 756422-07-8 XP-002593538.
Database Chemcats [Online], Chemical Abstracts Service, Columbus, Ohio, Sep. 23, 2009, TimTec Overseas Stock: "Order Nr OVC20768671", retrieved from STN Database accession No. 2034833097, Order Nr: OVS20768671=CAS Registry Nr: 904553-72-6; Order Nr: OVS20768677=CAS Registry Nr: 904553-76-0 XP-002593539.

(Continued)

Primary Examiner — Raymond Henley, III
(74) Attorney, Agent, or Firm — Ladas & Parry LLP

(57) ABSTRACT

Disclosed are nitrile derivatives and pharmaceutical compositions comprising nitrile derivatives. The pharmaceutical compositions comprise compounds of the formula I $$NC-(CH_2)_n-W-(CH_2)_m-Z-C\begin{pmatrix}N-R^1\\\|\\N-R^2\\|\\R^3\end{pmatrix}$$

and the pharmaceutically acceptable salts of such compounds. Also disclosed are processes for the preparation of such compounds, intermediates used in the preparation of such compounds, and the uses of such compounds in treating hyperproliferative diseases, inflammatory diseases and viral and bacterial infections and inducing apoptosis in cancer cells.

9 Claims, 9 Drawing Sheets

(56) References Cited

OTHER PUBLICATIONS

Database Chemcats [Online] Chemical Abstracts Service, Columbus, Ohio, Apr. 16, 2010, Rare Chemicals Screening Compounds: "Order Nr BG FC 1583". retrieved from STN Database accession No. 0008475877 Order Nr: BG FC 1583=Registry Nr: 717850-23-2 XP-002593540.
Database CA [Online] Chemical Abstracts Service, Columbus, Ohio, Dovlatyan, V. V. et al.: Reaction of ethylenethiourea with Halide functional derivatives:, retrieved from STN Database accession No. 2002:362.97 *abstract; compounds RN 63236-80-6. XP-002606846, (2002).
Database Chemcats [Online] Abstracts Service, Columbus, Ohio, Mar. 25, 2009, Florida Center for Heterocyclic Compounds Catalog: "Order Nr 1408", retrieved from STN, database accession No. 2000988314 *abstract XP-002606851.
Database Chemcats [Online] Abstracts Service, Columbus, Ohio, Sep. 23, 2009, TimTec Overseas Stock: "Order Nr OVS20768677", retrieved from STN database accession No. 2034833103 *abstract XP-002606853.
Database Chemcats [Online] Abstracts Service, Columbus, Ohio, Sep. 23, 2009, TimTec Overseas Stock: "Order Nr OVS21035900", retrieved from STN database accession No. 2095599101 * abstract XP-002606854.
Database Chemcats [Online] Abstracts Service, Columbus, Ohio, Apr. 16, 2010, Rare Chemicals Screening Compounds: "BG FC 1583", database accession No. 0008475877 *abstract XP-002606855.
Database Chemcats [Online] Abstracts Service, Columbus, Ohio, Mar. 10, 2010, Aurora Screening Library: "Order Nr K02.201.594", database accession No. 0009011410 * abstract XP-002606856.
Database Chemcats [Online] Abstracts Service, Columbus, Ohio, Sep. 23, 2009, TimTec Overseas Stock: "OVS20768680", retrieved from STN database accession No. 2034833106 * abstract XP-002606857.
Database Chemcats [Online] Abstracts Service, Columbus, Ohio, Sep. 23, 2009, TimTec Overseas Stock: "Order Nr OVS20768686", database accession No. 2034833112 * abstract XP-002606858.
Database Chemcats [Online] Abstracts Service, Columbus, Ohio, Mar. 10, 2010, Aurora Screening Library: "Order Nr K05.993.220", retrieved from STN database accession No. 00009045803 * abstract XP-002606859.
Database Chemcats [Online] Abstracts Service, Columbus, Ohio, Sep. 23, 2009, TimTec Overseas Stock: "OVS20768685", retrieved from STN database accession No. 2034833111 * abstract XP-002606860.
Database Chemcats [Online] Abstracts Service, Columbus, Ohio, Apr. 27, 2010, ASDI HTS Collections: "Order Nr 650001835", database accession No. 0008678898 * abstract XP-002606861.
Database Chemcats [Online] Abstracts Service, Columbus, Ohio, Sep. 23, 2009, TimTec Overseas Stock: Order Nr OVS002606862, retrieved from STN database accession No. 2095640591 * abstract XP-002606862.
Campaigne, E., et al., Reactions of ethylenethiourea with .alpha.- and .beta.-halo acids and derivatives, *Journal of Organic Chemistry* vol. 29, No. 7, 1964•, pp. 1715-1719 ISSN: 0022-3263 * abstract XP-00259535.
Keillor, J.W., et al., "Attack of Zwitterionic Ammonium Thiolates on a Distorted Anilide as a Model for the Acylation of Papain by Amides. A Simple Demonstration of a Bell-shaped pH/Rate Profile," *Journal of the American Chemical Society*, vol. 114, No. 21, 1992, pp. 7983-7984, paragraph bridging left hand and right hand column, ISSN: 0002-7863. XP-002593536.
Klimesova, Vera, et al., "Synthesis of 2-benzylthiopyridine-4-carbothioamide derivatives and their antimycobacterial, antifungal and photosynthesis-inhibiting activity," *Eurogean Journal of Medicinal Chemistry, Editions Scientifique, Elsevier*, Paris, France, vol. 3, No. 5, May 1, 1999, pp. 433-440, ISSN : 0223-5234, figure 1.
Klimesova, Vera, et al., "New pyridine derivatives as potential antimicrobial agents,"*Elsevier, Il Farmaco (Lausanne)*, vol. 54, No. 10, Oct. 30, 1999, pp. 666-672, ISSN: 0014-827X, scheme 1 and 2 XP-002606843.
Usova, et al., "Synthesis of 5-(5-substituted 2-furyl)thiazole derivatives by reaction of 2-(5-substituted furfuryl)thiuronium salts and acetic anhydride," *Himia Geterosciklieskih Soedinenij—Chemistry of Heterocyclic Compounds, Latvijskij Institut Organiceskogo Sinteza, Riga, LV*, No. 4, Jan. 1, 1990, pp. 557-562, ISSN:0132-6244, scheme on p. 557. XP-009095544.
Masquelin, T., et al., "A facile preparation of a combinatorial library of 2,6-disubstituted triazines," *Tetrahedron letters, Elsevier, Amsterdam, NL LNKD-*, vol. 39, No. 32, Aug. 6, 1998, pp. 5725-5726, ISSN: 0040-4039, scheme 1.
Reinhart, Francis, E., et al., "Screening of compounds for antitumor activity. Effects of some substituted pyridines on the growth of Walker carcinosarcoma 256 in tissue culture," *Journal of the Franklin Institute*, vol. 261, 1956, pp. 669-670, table 1. XP-002593534.
Bierer, D.E., et a., "Novel 1,2-dithiins: Synthesis, Molecular Modeling Studies, and Antifungal Activity," *Journal of Medicinal Chemistry, American Chemical Society, Washington*, vol. 38, No. 14, Jul. 17, 1985, pp. 2628-2648, ISSN: 0022-2623, p. 2629, scheme 2, compound 6. XP-002173882.
Masquelin T., et al., "A Novel Solution- and Solid-Phase Approach to 2,4,5-Tri- and 2,4,5,6-Tetra-substituted Pyrimidines and Their Conversion into Condensed Heterocycles," *Helvetica Chimica Acta*, Basel, vol. 81, No. 4, Jan. 1, 1998, pp. 646-660 ISSN: 018-019x, p. 647, compound 3e. XP-009003856.
Radics, U., et al., "Synthesis of 4-([omegaJ-Aminoalkyl)- or 4-([omega]-Lactamiminoalky)thiazoles by Ring Chain Transformation of sothioureas with Lactam Derivatives," *Synthesis*, No. 7, 1992, pp. 673-677, ISSN: 0039-7881, p. 674, compound 1f. XP-002606847.
Schmidpeter, Alfred et al., "Four- and five-membered phosphorus heterocycles 65. 1,3,4-Thiazaphosphole," Angewandte Chemie vol. 97, No. 2, 1985 ,pp. 125-127, p. 126, compound 3 f. XP-002606848.
Yokoyama, Masataka et al., The reaction of thiourea with carbon disulfide, *Tetrahedron Letterss*, 21(7), 635-6, Codeni Teleay; ISSN: 0040-4039, 1980, compounds 10a and 10. XP-002606844.
Lukes, R., et all., "Syntheses in the allo-lupinane series.IV. An alternative synthesis of 4-hydroxymethylquinolizidine," *Collection of Czechoslovak Chemical Communications*, vol. 24, 1959, pp. 2318-2323, p. 2320, paragraph entitled y-(1 Cyano-2-piperidyl)propylbromid (III).
Vinsova, Jarmila, et al., "Antituberculosis agents. XL VIII. Preparation of symmetrical and asymmetrical dipyridyl sulfides substituted on the ring," *Folia Pharmaceutica Universitatis Carolinae* vol. 1998, No. 15, 1990, pp. 15-17, sheme 3 on p. 17 and scheme 6 on p. 19. XP-009140456.
Stacy, Gardner W., et al., "A Tautomeric Nitrile-Thiol Iminothiolactone System," Journal of Organic Chemistry, 29(3), 607-12, ISSN: 0022-3263, 1964, p. 609, compound XV. XP-002606852.
Fromm, E., et al., "Derivatives of Persulphocyanic Acid and of Cyanaminodithiocarbonic Acid. Synthesis of New Triazoles," *Justus Liebig Annalen Der Chemie.*, vol. 355, 1908, pp. 196-215, compounds according to formulae on p. 200, 201 (bottom part), 202 (middle part), 203 (upper part, 204 (upper part. (1972).
Miller, Ellis et al., "The Preparation of Some Amino Sulfonamides" *Journal of the American Chemical Society*, vol. 62, 1940, pp. 2099-2102, ISSN: 0002-7863, p. table I XP002593537.

* cited by examiner

NITRILE DERIVATIVES AND THEIR PHARMACEUTICAL USE AND COMPOSITIONS

CROSS-REFERENCE APPLICATIONS

This application is a continuation of U.S. patent application Ser. No. 12/780,132 filed May 14, 2010 (now granted as U.S. Pat. No. 8,338,454) which claims the benefit of U.S. Provisional Patent Application Ser. No. 61/180,121, filed May 20, 2009, the content of which is incorporated herein by reference.

BACKGROUND OF THE INVENTION

The present invention relates to nitrile derivatives and to pharmaceutical compositions comprising nitrile derivatives. The invention also relates to the pharmaceutically acceptable salts of such compounds, processes for the preparation of such compounds, intermediates used in the preparation of such compounds, and the uses of such compounds in treating hyperproliferative diseases, inflammatory diseases and viral and bacterial infections.

The aforementioned derivatives and their pharmaceutically acceptable salts have one or more of the following properties: AKT inhibition, inhibition of cell cycle hyperproliferation, cell cycle specific induction of apoptosis in cancer cells, inhibition of $LTB_4$ activities, and antiangiogenic activities showing significant reduction in tumor size in experimental animals. These compounds are, therefore, useful in the treatment of a wide range of disorders in mammals, including, but not limited to hyperproliferative diseases, such as head and neck cancer, including gliomas, drug resistant lung cancer, estrogen dependent or non-dependent cancers in humans, non-small cell lung cancer and colon cancer. Non-limiting examples of estrogen dependent cancers are breast cancer and ovarian cancer. As a result of their inhibition of $LTB_4$ activities, these compounds are useful in treating inflammatory diseases such as allergy, asthma and arthritis, and as a result of their AKT inhibition and cytokine activation, these compounds are also useful in treating viral and bacterial infections. There is currently great interest in finding new therapies for the foregoing diseases.

Salts of substituted isothiourea compounds are referred to in Miller et al., JACS, Vol. 62, 2099-2103 (1940); Shapiro, et al., Radiation Research, Vol. 7, No. 1, 22-34 (1957); King et al., Biochemistry, Vol. 17, No. 8, 1499-1506 (1978); Bauer and Welsh, J. Org. Chem. Vol. 26, No. 5, 1443-1445 (1961); Southan, et al., Br. J. Pharmacol., Vol. 114, 510-516 (1995); and Gerber, et al., Organic Synthesis, Vol. 77, 186 (2000).

SUMMARY OF THE INVENTION

In a particular embodiment, the present invention relates to a pharmaceutical composition for treating hyperproliferative diseases, including but not limited to cancer, inflammatory diseases and viral and bacterial infections in mammals, including, but not limited to, humans, comprising an antihyperproliferative disease, anti-inflammatory, antiviral or antibacterial effective amount of a compound of formula I

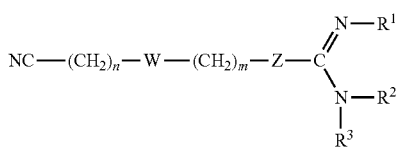

wherein, Z is selected from sulphur, copper, silver, gold and platinum, or Z is a halogen-containing moiety selected from $ClO_2$, $BrO_2$, and $IO_2$;

wherein n is zero or an integer from 1 to 8 and m is zero or an integer from 1 to 8;

$R^1$, $R^2$ and $R^3$ are independently selected from hydrogen, —$CH_2$-cyclohexyl, $C_1$-$C_6$ alkyl, $C_2$-$C_6$ alkenyl, and $C_2$-$C_6$ alkynyl, wherein the alkyl moieties of said alkyl, alkenyl and alkynyl groups may be linear, branched and cyclic and combinations of linear, branched and cyclic alkyl, alkenyl and alkynyl moieties and said groups may be substituted with groups selected from methyl, ethyl, propyl, isopropyl, n-butyl, t-butyl, methoxy, ethoxy, O-n-propyl, O-isopropyl, O-n-butyl, and O-t-butyl; or $R^1$ and $R^2$, taken together with the nitrogens to which they are directly attached and the carbon which is attached to the nitrogens, form a five or more membered ring, wherein p is an integer from 1 to 7 as shown below

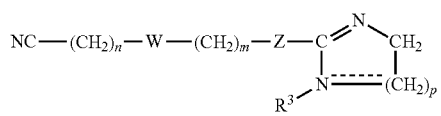

wherein the broken line represents an optional double bond, with the proviso that when there is such a double bond. $R^3$ is absent and the $CH_2$ group adjacent to the double bond has one hydrogen rather than two hydrogens, or $R^2$ and $R^3$ taken together with the nitrogen to which they are attached form a three or more membered ring, wherein p is an integer from 1 to 7, as shown below

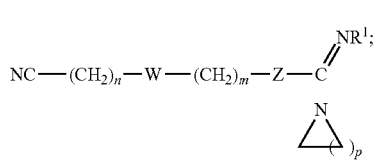

W is absent or W is selected from
—$CH_2$—, —$CH_2$—$CH_2$—, trans —CH═CH—, cis —CH═CH—, —C≡C—, or —$CHR^4$—$CHR^5$—, trans —$CR^4$═$CR^5$—, cis —$CR^4$═$CR^5$—, wherein $R^4$, and $R^5$ are independently selected from —$CH_2$-cyclohexyl, $C_1$-$C_6$ alkyl, $C_2$-$C_6$ alkenyl, $C_2$-$C_6$ alkynyl, and $C_1$-$C_6$ alkyl ether (also referred to as $C_1$-$C_6$ alkyl-O—); or W is a disubstituted moiety, wherein the term disubstituted is used to indicate how W is attached to the groups $(CH_2)_m$ and $(CH_2)_n$, selected from the group of disubstituted moieties consisting of (a) a 1,2-, 1,3-, or 1,4-disubstituted six membered ring which may be saturated or unsaturated with one, two or three double bonds; a 1,2-, or 1,3-disubstituted five membered ring which may be saturated or unsaturated with one or two double bonds; a 1,2-, or 1,3-disubstituted four membered ring which may be saturated or unsaturated with one or two double bonds; or a 1,2-disubstituted three membered ring which may be saturated and unsaturated with a double bond as shown by the following formulas, wherein the substituents on said disubstituted rings are the groups attached to W in formula I

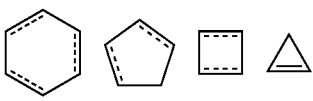

wherein the broken lines indicate optional double bonds;
(b) a 1,2-, 1,3-, or 1,4-disubstituted six membered ring which may be saturated or unsaturated with one, two or three double bonds; a 1,2-, or 1,3-disubstituted five membered ring which may be saturated or unsaturated with one or two double bonds; a 1,2-, or 1,3-disubstituted four membered ring which may be saturated or unsaturated with one or two double bonds; or a 1,2-disubstituted three membered ring which may be saturated and unsaturated with a double bond as shown by the following formulas, wherein the substituents on said disubstituted rings are the groups attached to W in formula I, and said disubstituted rings may have additional substituents $R^6$, $R^7$, $R^8$, and $R^9$ as shown in the following formulas

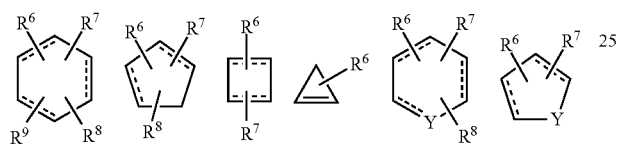

wherein the broken lines indicate optional double bonds; wherein $R^6$, $R^7$, $R^8$ and $R^9$ are independently selected from hydrogen, —$CH_2$-cyclohexyl, $C_1$-$C_6$ alkyl, $C_2$-$C_6$ alkenyl, $C_2$-$C_6$ alkynyl, or $C_1$-$C_6$ alkyl ether; the six membered ring may be saturated or have one, two or three double bonds, the five and four membered rings may be saturated or have one or two double bonds and the three membered ring may be saturated or have one double bond; wherein Y is nitrogen, oxygen, or sulphur;
(c) a ring selected from 1,2-, 1,3-, 1,4-, 1,5-, 1,6-, or 1,7-disubstituted saturated and unsaturated nine membered rings with one or more double bonds, with ring positions numbered as shown in the first ring set forth below, said ring selected from the second to the thirteenth rings set forth below, wherein the substituents on said disubstituted rings are the groups attached to W in formula I, and said disubstituted rings may have additional substituents $R^6$, $R^7$, $R^8$, $R^9$ and $R^{10}$ as shown in the following formulas

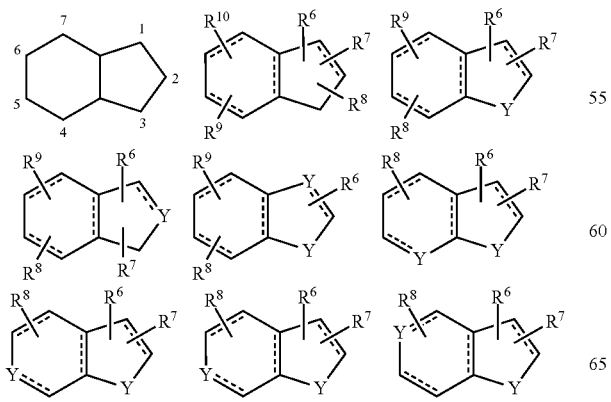

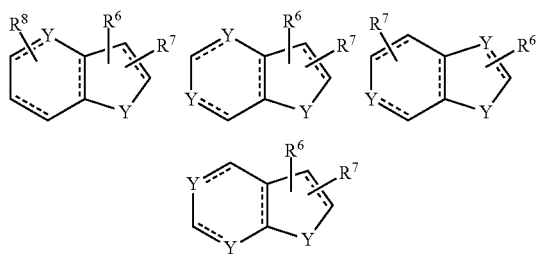

wherein the broken lines indicate optional double bonds;
wherein $R^6$, $R^7$, $R^8$, $R^9$, and $R^{10}$ are independently selected from hydrogen, —$CH_2$-cyclohexyl, $C_1$-$C_6$ alkyl, $C_2$-$C_6$ alkenyl, $C_2$-$C_6$ alkynyl, or $C_1$-$C_6$ alkyl ether; wherein Y is nitrogen, oxygen, or sulphur;
(d) a ring selected from 1,2-, 1,3-, 1,4-, 1,5-, 1,6-, 1,7-, or 1,8-disubstituted saturated and unsaturated naphthalene rings with one or more double bonds, with ring positions numbered as shown in the first ring set forth below, said rings selected from the second to sixth rings set forth below, wherein the substituents on said disubstituted rings are the groups attached to W in formula I, and said disubstituted rings may have additional substituents $R^6$, $R^7$, $R^8$, $R^9$, $R^{10}$ and $R^{11}$ as shown in the following formulas

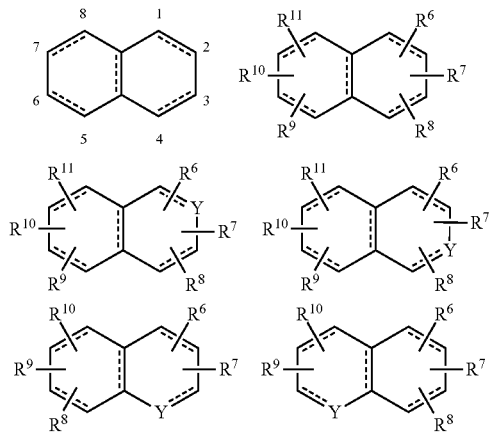

wherein the broken lines indicate optional double bonds; wherein $R^6$, $R^7$, $R^8$, $R^9$, $R^{10}$ and $R^{11}$ are independently selected from hydrogen, —$CH_2$-cyclohexyl, $C_1$-$C_6$ alkyl, $C_2$-$C_6$ alkenyl, $C_2$-$C_6$ alkynyl, or $C_1$-$C_6$ alkyl ether; wherein Y is nitrogen, oxygen, or sulphur; and
(e) a ring selected from 1,2-, 1,3-, 1,4-, 1,5-, 1,6-, 1,7-, 1,8-, 1,9-, 1,10-, 2,5-, 3,5-, 4,5-, or 5,10-disubstituted saturated and unsaturated anthracene rings with one or more double bonds, with ring positions numbered as shown in the first ring set forth below, said ring selected from the second to ninth rings set forth below, wherein the substituents on said disubstituted rings are the groups attached to W in formula I, and said disubstituted rings may have additional substituents $R^6$, $R^7$, $R^8$, $R^9$, $R^{10}$, $R^{11}$, $R^{12}$ and $R^{13}$ as shown in the following formulas

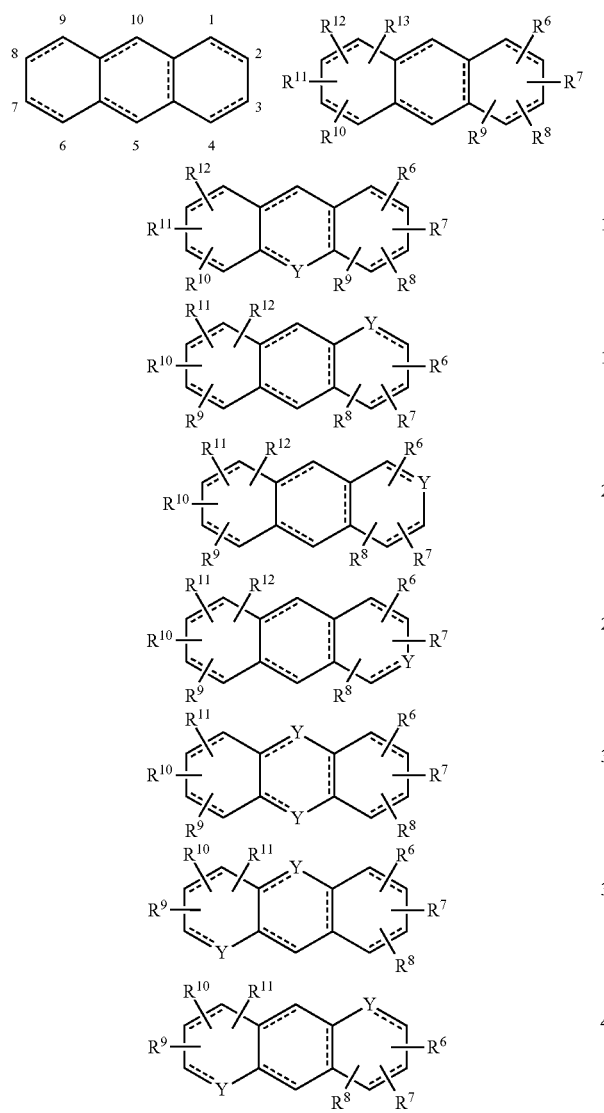

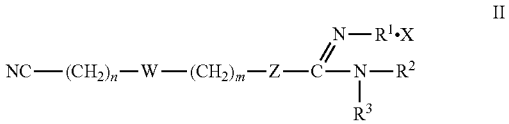

wherein the broken lines indicate optional double bonds;
wherein $R^6$, $R^7$, $R^8$, $R^9$, $R^{10}$, $R^{11}$, $R^{12}$, and $R^{13}$ are independently selected from hydrogen, —$CH_2$-cyclohexyl, $C_1$-$C_6$ alkyl, $C_2$-$C_6$ alkenyl, $C_2$-$C_6$ alkynyl, or $C_1$-$C_6$ alkyl ether; wherein Y is nitrogen, oxygen, or sulphur;
or a pharmaceutically acceptable salt thereof and a pharmaceutically acceptable carrier.

In one embodiment $R^1$, $R^2$ and $R^3$ are independently selected from hydrogen, methyl, ethyl, n-propyl, isopropyl, cyclopropyl, —$CH_2$-cyclopropyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl, ethenyl, propenyl, butenyl, 1-methyl-2-buten-1-yl, ethynyl, 2-propynyl (propargyl), and 1-propynyl, which may bear one or more substituents selected from methyl, ethyl, propyl, isopropyl, n-butyl, t-butyl, methoxy, ethoxy, O-n-propyl, O-isopropyl, O-n-butyl, and O-t-butyl.

In a one embodiment of the invention, the compound of formula I is a compound of formula II wherein n, m, W, Z, $R^1$, $R^2$, and $R^3$ are as defined above and X is a pharmaceutically acceptable acid. In one embodiment the acid is HCl. In another embodiment the acid is HBr.

In one embodiment of the invention, Z is sulfur, copper, silver, gold or platinum. In another embodiment of the invention, Z is sulfur. In another embodiment of the invention, Z is copper. In another embodiment of the invention, Z is gold. In another embodiment of the invention, Z is a halogen-containing moiety as defined above. In another embodiment of the invention, $R^1$, $R^2$ and $R^3$ are each hydrogen. In one specific compound of the invention, Z is copper, $R^1$, $R^2$ and $R^3$ are each hydrogen, m is 1, n is 1, and W is $CH_2$.

In one embodiment of the invention, $R^4$, $R^5$, $R^6$, $R^7$, $R^8$, $R^9$, $R^{10}$, $R^{11}$, $R^{12}$, and $R^{13}$ are independently selected from hydrogen, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl, ethenyl, propenyl, butenyl, 1-methyl-2-buten-1-yl, ethynyl, 2-propynyl (propargyl), and 1-propynyl, which may bear one or more substituents selected from methyl, ethyl, propyl, isopropyl, n-butyl, t-butyl, methoxy, ethoxy, O-n-propyl, O-isopropyl, O-n-butyl, and O-t-butyl.

In one embodiment of the invention W is allyl or vinyl.

One embodiment of the present invention relates to a pharmaceutical composition for the treatment of hyperproliferative diseases, including but not limited to cancer, inflammatory diseases, and viral and bacterial infections in mammals comprising an antihyperproliferative disease, antiinflammatory, antiviral or antibacterial effective amount of 4-isothioureidobutyronitrile (also named S-(3-cyanopropyl)isothiourea or S-(γ-cyanopropyl)lisothiourea) or a pharmaceutically acceptable salt thereof and a pharmaceutically acceptable carrier. In a particular embodiment, the composition comprises the hydrochloride acid addition salt of 4-isothioureidobutyronitrile which is also known as "Kevetrin". This salt has the following formula

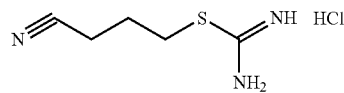

Kevetrin

In another embodiment the composition comprises the hydrobromide acid addition salt of 4-isothioureidobutyronitrile.

In another embodiment the present invention relates to a pharmaceutical composition for the treatment of hyperproliferative diseases, including but not limited to cancer, inflammatory diseases, and viral and bacterial infections in mammals comprising an antihyperproliferative disease, antiinflammatory, antiviral or antibacterial effective amount of a compound selected from S-(2-cyanoethyl)isothiourea, S-(4-cyanobutyl)isothiourea, S-(5-cyanopentyl)isothiourea or a pharmaceutically acceptable salt thereof and a pharmaceutically acceptable carrier.

In another embodiment the present invention relates to a pharmaceutical composition for the treatment of hyperproliferative diseases, including but not limited to cancer, inflammatory diseases, and viral and bacterial infections in mammals comprising an antihyperproliferative disease, anti-inflammatory, antiviral or antibacterial effective amount of a compound selected from S-(4-cyanomethylphenyl)methylisothiourea hydrochloride, S-2(4-[2-cyanoethyl]phenyl) ethylisothiourea mesylate, S-(2-cyanomethylphenyl)methylisothiourea hydrochloride, S-(6-cyanomethylpyridin-2-yl) methylisothiourea hydrochloride, S-(3-cyanomethylphenyl) methylisothiourea hydrochloride, S-(1-cyanomethylnaphth-2-yl))methylisothiourea hydrochloride or a different pharmaceutically acceptable salt thereof and a pharmaceutically acceptable carrier. In another embodiment, the pharmaceutical composition comprises a compound selected from the compounds prepared as described in Example 11 set forth below or a different pharmaceutically acceptable salt thereof or a free base thereof and a pharmaceutically acceptable carrier.

In one embodiment of the invention the pharmaceutical composition does not include S-cyanomethylisothiourea HBr. In another embodiment of the invention the pharmaceutical composition does not include S-cyanomethylisothiourea HCl or S-cyanomethylisothiourea HBr. In another embodiment of the invention the pharmaceutical composition does not include pharmaceutically acceptable salts of S-cyanomethylisothiourea. In another embodiment of the invention the pharmaceutical composition does not include S-cyanomethylisothiourea as the free base or as a salt.

In one embodiment of the invention the pharmaceutical composition does not include S-(2-cyanoethyl)isothiourea HCl, S-cyanomethylisothiourea HBr and S-cyanomethylisothiourea HCl. In another embodiment of the invention the pharmaceutical composition does not include S-(2-cyanoethyl)isothiourea HCl, S-(2-cyanoethyl)isothiourea HBr, S-cyanomethylisothiourea HCl or S-cyanomethylisothiourea HBr. In another embodiment of the invention the pharmaceutical composition does not include pharmaceutically acceptable salts of S-(2-cyanoethyl)isothiourea and S-cyanomethylisothiourea. In another embodiment of the invention the pharmaceutical composition does not include S-(2-cyanoethyl)isothiourea as the free base or as a salt and does not include S-cyanomethylisothiourea as the free base or as a salt.

In another embodiment of the present invention the pharmaceutical composition does not include S-(cyanomethyl) isothiourea HCl, S-(cyanomethyl)isothiourea HBr, S-(2-cyanoethyl)isothiourea HCl, S-(2-cyanoethyl)isothiourea HBr, S-(2-cyanoethyl)isothiourea p-toluenesulfonate, S-(3-cyanopropyl)isothiourea HCl, S-(3-cyanopropyl)isothiourea picrate, and S-para-cyanobenzylisothiourea HCl. In another embodiment of the present invention the pharmaceutical composition also does not include the hydrobromide salt of S-(3-cyanopropyl)isothiourea or S-para-cyanobenzylisothiourea.

In another embodiment of the present invention the pharmaceutical composition does not include a pharmaceutically acceptable salt of S-(cyanomethyl)isothiourea, S-(2-cyanoethyl)isothiourea, S-(3-cyanopropyl)isothiourea, or S-para-cyanobenzylisothiourea. In another embodiment of the invention the compound is not selected from S-(cyanomethyl) isothiourea. S-(2-cyanoethyl) isothiourea, S-(3-cyanopropyl) isothiourea and S-para-cyanobenzylisothiourea and pharmaceutically acceptable salts thereof.

The pharmaceutically acceptable salts of the compounds of formula I include the acid addition and base salts (including disalts) thereof. Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. For a review on suitable salts, see "Handbook of Pharmaceutical Salts Properties, Selection, and Use" by Stahl and Wermuth (Wiley-VCH, Weinheim, Germany, 2002).

A pharmaceutically acceptable salt of a compound of formula I may be readily prepared by mixing together solutions of the compound of formula I and the desired acid or base, as appropriate. The salt may precipitate from solution and be collected by filtration or may be recovered by evaporation of the solvent. The degree of ionisation in the salt may vary from completely ionised to almost non-ionised.

The compounds of formula I and the pharmaceutically acceptable salts thereof (hereinafter also referred to as the active compounds) may exist in both unsolvated and solvated forms. The active compounds (including, those in the form of salts, free bases, free acids and neutral compounds) may form hydrates and other solvates. The term 'solvate' is used herein to describe a molecular complex comprising a compound of the invention and one or more pharmaceutically acceptable solvent molecules, for example, ethanol. The term 'hydrate' is employed when said solvent is water. Pharmaceutically acceptable solvates include hydrates and other solvates wherein the solvent of crystallization may be isotopically substituted, e.g. $D_2O$, $d_6$-acetone, $d_6$-DMSO. The active compounds may exist as clathrates or other complexes. In general, the solvated, hydrated and the like forms are equivalent to the unsolvated, unhydrated/anhydrous and the like forms and the compounds, compositions and uses claimed herein are intended to encompass these forms, as well as the isomeric, crystalline and amorphous forms and the isotopically labeled compounds discussed below, within the scope of the present invention.

Compounds of formula I containing one or more asymmetric carbon atoms can exist as two or more stereoisomers. Where a compound of formula I contains an alkenyl or alkenylene group or a cycloalkenyl group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism. The compounds of formula I may also exist as isomers if they form acid addition or base salts wherein the counterion is optically active, for example, D-lactate or L-lysine, or racemic, for example, DL-tartrate or DL-arginine.

Mixtures of stereoisomers may be separated by conventional techniques known to those skilled in the art. See, for example, "Stereochemistry of Organic Compounds" by E. L. Eliel (Wiley, New York, 1994).

Cis/trans isomers may be separated by conventional techniques well known to those skilled in the art, for example, chromatography and fractional crystallisation.

In general, enantiomerically pure compounds of the present invention can be prepared and can be isolated according to art-known processes such as, for example, chiral synthesis from a suitable optically pure precursor and resolution of a racemate (or a racemate of a salt or derivative). For example, a racemate (or a racemic precursor) may be separated using chiral high pressure liquid chromatography (HPLC). Alternatively, a racemate (or a racemic precursor) may be reacted with a suitable optically active compound, for example, an alcohol, or, in the case where the compound of formula I contains an acidic or basic moiety, with an acid or base such as tartaric acid or 1-phenylethylamine. The resulting diastereomeric mixture may be separated by chromatography or fractional crystallization or both and one or both of the diastereoisomers may be converted to the corresponding pure enantiomer(s) by means well known to a skilled person.

Chiral compounds of the present invention (and chiral precursors thereof) may be obtained in enantiomerically-enriched form using chromatography, typically HPLC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

In the solid state, the compounds of the present invention may exist in crystalline or amorphous form.

The present invention includes all pharmaceutically acceptable isotopically-labelled compounds of formula I claimed herein wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{38}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically-labelled compounds of formula I, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labelled compounds of formula I can generally be prepared by conventional techniques known to those skilled in the art or by processes analogous to those described in the accompanying Examples using an appropriate isotopically-labeled reagent in place of the non-labeled reagent previously employed.

The present invention also relates to a pharmaceutical composition for the treatment of cellular hyperproliferation comprising an antihyperproliferation effective amount of a compound of formula I or a pharmaceutically acceptable salt thereof and a pharmaceutically acceptable carrier. In another embodiment, the present invention relates to a pharmaceutical composition for the treatment of cancer comprising an anticancer effective amount of a compound of formula I or a pharmaceutically acceptable salt thereof and a pharmaceutically acceptable carrier. In another embodiment, the present invention relates to a pharmaceutical composition for the treatment of cancer comprising an apoptosis inducing effective amount of a compound of formula I or a pharmaceutically acceptable salt thereof and a pharmaceutically acceptable carrier. In other embodiments, one or more of the compounds excluded from the pharmaceutical compositions discussed above may be excluded from the pharmaceutical compositions referred to in this paragraph as well.

The present invention also relates to a pharmaceutical composition in dosage unit form for the treatment of cellular hyperproliferation, including but not limited to cancer, comprising an antihyperproliferation or anticancer effective amount of a compound of formula I or a pharmaceutically acceptable salt thereof and a pharmaceutically acceptable carrier. In other embodiments, one or more of the compounds excluded from the pharmaceutical compositions discussed above may be excluded from the aforementioned pharmaceutical composition as well.

The present invention also relates to a parenteral pharmaceutical composition for the treatment of cellular hyperproliferation, including but not limited to cancer, comprising an antihyperproliferation or anticancer effective amount of a compound of formula I or a pharmaceutically acceptable salt thereof and a pharmaceutically acceptable carrier suitable for parenteral administration. The pharmaceutical product can be obtained by dissolving a desired quantity of the product in a sterile isotonic solution which can be readily administered through any desired route. In other embodiments, one or more of the compounds excluded from the pharmaceutical compositions discussed above may be excluded from the aforementioned pharmaceutical composition as well.

The present invention also relates to a method of treating hyperproliferative diseases, including but not limited to cancer, inflammatory diseases, and viral and bacterial infections in mammals, including humans, comprising administering to a patient in need of such treatment an antihyperproliferative disease, anti-inflammatory, antiviral or antibacterial effective amount of a compound of formula I or a pharmaceutically acceptable salt thereof. In one embodiment the compound is selected from S-(3-cyanopropyl)isothiourea, S-(2-cyanoethyl)isothiourea, S-(4-cyanobutyl)isothiourea, S-(5-cyanopentyl)isothiourea, S-(4-cyanomethylphenyl) methylisothiourea, S-2(4-[2-cyanoethyl]phenyl)ethylisothiourea, S-(2-cyanomethylphenyl) methylisothiourea, S-(6-cyanomethylpyridin-2-yl)methylisothiourea. S-(3-cyanomethylphenyl) methylisothiourea, and S-(1-cyanomethylnaphth-2-yl))methylisothiourea and the pharmaceutically acceptable salts thereof. In another embodiment the compound is S-(3-cyanopropyl)isothiourea hydrochloride. In another embodiment the compound is selected from the compounds prepared as described in Example 11 below, or a different pharmaceutically acceptable salt thereof or a free base thereof.

The present invention also relates to a method of treating hyperproliferation comprising administering to a patient in need of such treatment an antihyperproliferation effective amount of a compound of formula I or a pharmaceutically acceptable salt thereof. In another embodiment, the present invention relates to a method of treating cancer comprising administering to a patient in need of such treatment an anticancer effective amount of a compound of formula I or a pharmaceutically acceptable salt thereof. In another embodiment, the present invention relates to a method of treating cancer comprising administering to a patient in need of such treatment an apoptosis inducing effective amount of a compound of formula I or a pharmaceutically acceptable salt thereof. In other embodiments, one or more of the compounds excluded from the pharmaceutical compositions discussed above may be excluded from the methods referred to in this paragraph as well.

The present invention also relates to a method of treating head and neck cancer, non-small cell lung cancer, small cell lung cancer, resistant types of lung and any female cancers, ovarian cancer, breast cancer or colon cancer in a mammal in need of such treatment comprising administering to said mammal an anticancer effective amount of a compound of formula I or a pharmaceutically acceptable salt thereof.

In one embodiment of the present invention the cancer is selected from head and neck cancer, non-small cell lung cancer, ovarian cancer and colon cancer. In one embodiment of the present invention the head cancer is a glioma.

The present invention also relates to a method of treating a hyperproliferative disease responsive to induction of apoptosis in a mammal in need of such treatment comprising administering separately, simultaneously, concurrently, sequentially or chronologically staggered to said mammal in need thereof, an amount of an active compound, which is a compound of formula I or a pharmaceutically acceptable salt thereof and an amount of at least one second compound or radiation, said second compound being an anti-cancer agent selected from the group consisting of chemotherapeutic anti-cancer agents and target-specific anti-cancer agents, wherein the amounts of the active compound and said second compound or radiation result in a therapeutic effect. In one embodiment of the invention, said second compound is selected from the group consisting of (i) alkylating/carbamylating agents; (ii) platinum derivatives; (iii) antimitotic agents/tubulin inhibitors; (iv) topoisomerase inhibitors; (v) pyrimidine antagonists; (vi) purine antagonists; (vii) folic acid antagonists; and (viii) injected radioactive materials. In one embodiment of the invention, said target-specific anti-cancer agent is selected from the group consisting of (i) kinase inhibitors; (ii) proteasome inhibitors; (iii) histone deacetylase inhibitors; (iv) heat shock protein 90 inhibitors; (v) vascular targeting agents (VAT) anti-angiogenic drugs, and KDR tyrosine kinase inhibitors; (vi) monoclonal antibodies as well as mutants and conjugates of monoclonal antibodies and antibody fragments; (vii) oligonucleotide based therapeutics; (viii) Toll-like receptor/TLR 9 agonists, TLR 7 agonists and analogues thereof, or TLR 7/8 agonists as well as immunostimulatory RNA as TLR 7/8 agonists; (ix) protease inhibitors; (x) hormonal therapeutics; (xi) bleomycin; (xii) retinoids; (xiii) DNA methyltransferase inhibitors; (xiv) alanosine; (xv) cytokines; (xvi) interferons; and (xvii) death receptor agonists. In one embodiment of the invention, said compound of formula I or a pharmaceutically acceptable salt thereof is administered separately, simultaneously, concurrently, sequentially or chronologically staggered with an anti-cancer effective amount of radiation. It will be clear from the foregoing that as used herein the term "effective amount" includes an amount of an active compound that is effective when administered by itself as well as an amount of an active compound that is effective when administered in conjunction with another therapeutic agent.

The hyperproliferative diseases that may be treated by the methods of the present invention include, but are not limited to, cancer of the breast, bladder, bone, brain, central and peripheral nervous system, colon, endocrine glands, esophagus, endometrium, germ cells, head and neck, kidney, liver, lung, larynx and hypopharynx, mesothelioma, sarcoma, ovary, pancreas, prostate, rectum, small intestine, soft tissue, testis, stomach, skin, ureter, vagina and vulva; inherited cancers, retinoblastoma and Wilms tumor; leukemia, lymphoma, non-Hodgkins disease, chronic and acute myeloid leukemia, acute lymphoblastic leukemia, Hodgkins disease, multiple myeloma and T-cell lymphoma; myelodysplastic syndrome, plasma cell neoplasia, paraneoplastic syndromes, cancers of unknown primary site, drug resistant cancers and AIDS related malignancies and the disease is treated by administering to a mammal in need of such treatment an antihyperproliferation or anticancer effective amount of a compound of formula I or a pharmaceutically acceptable salt thereof. In one embodiment of the invention, the hyperproliferative disease is selected from the group consisting of head and neck cancer, non-small cell lung cancer, small cell lung cancer, resistant types of lung and any female cancers, breast cancer, ovarian cancer and colon cancer.

The present invention also relates to a compound of the formula I as defined above or a pharmaceutically acceptable salt thereof with the proviso that the compound is not S-(cyanomethyl)isothiourea HCl, S-(cyanomethyl)isothiourea HBr, S-(2-cyanoethyl)isothiourea HCl, S-(2-cyanoethyl)isothiourea HBr, S-(2-cyanoethyl)isothiourea p-toluenesulfonate, S-(3-cyanopropyl)isothiourea HCl, S-(3-cyanopropyl)isothiourea picrate, and S-para-cyanobenzylisothiourea HCl. In another embodiment of the present invention the compound is also not a hydrobromide salt of S-(3-cyanopropyl)isothiourea or S-para-cyanobenzylisothiourea.

In another embodiment of the present invention the compound is not a pharmaceutically acceptable salt of S-(cyanomethyl)isothiourea, S-(2-cyanoethyl)isothiourea, S-(3-cyanopropyl) isothiourea, or S-para-cyanobenzylisothiourea. In another embodiment of the invention the compound is not selected from S-(cyanomethyl)isothiourea, S-(2-cyanoethyl)isothiourea, S-(3-cyanopropyl)isothiourea and S-para-cyanobenzylisothiourea and pharmaceutically acceptable salts thereof.

It should be noted that S-cyanomethylisothiourea is also named Carbamimidothioic acid, cyanomethyl ester; S-(2-cyanoethyl)isothiourea is also named Carbamimidothioic acid, cyanoethyl ester; S-(3-cyanopropyl)isothiourea is also named Carbamimidothioic acid, cyanopropyl ester; and S-para-cyanobenzylisothiourea is also named Carbamimidothioic acid, (4-cyanophenyl) methyl ester.

In one embodiment of the present invention the compound is selected from S-(4-cyanobutyl) isothiourea and S-(5-cyanopentyl)isothiourea and pharmaceutically acceptable salts thereof. In another embodiment of the present invention the compound is selected from, S-(4-cyanomethylphenyl)methylisothiourea hydrochloride, S-2(4-[2-cyanoethyl]phenyl)ethylisothiourea mesylate, S-(2-cyanomethylphenyl)methylisothiourea hydrochloride, S-(6-cyanomethylpyridin-2-yl)methylisothiourea hydrochloride, S-(3-cyanomethylphenyl)methylisothiourea hydrochloride, S-(1-cyanomethylnaphth-2-yl))methylisothiourea hydrochloride or different pharmaceutically acceptable salts thereof. In another embodiment the compound is selected from the compounds prepared as described in Example 11 set forth below or different pharmaceutically salt thereof or a free base thereof.

The present invention also relates to a process for preparing the hydrochloride acid addition salt of a compound of the formula I wherein Z is sulfur comprising reacting thiourea or a thiourea derivative of the formula

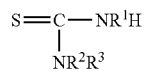

wherein $R^1$, $R^2$ and $R^3$ are as defined above for formula I with the appropriate nitrile derivative of the formula NC—$(CH_2)_n$—W—$(CH_2)_m$Cl, wherein n, m, and W are as defined above for the compound of the formula I, in water or water/alcohol solvent or in a polar solvent, at reflux temperature to afford the compound of formula I wherein Z is sulfur, and, if desired, preparing the free base or a different acid addition salt. In one embodiment of the invention the solvent is selected from an alcohol selected from methanol, ethanol, isopropanol and mixtures of one or more of the foregoing alcohols with water.

The present invention also relates to a process for preparing the hydrochloride acid addition salt of a compound of formula I wherein Z is selected from copper, silver, gold, platinum, and halogen-containing moieties selected from $ClO_2$, $BrO_2$ and $IO_2$ comprising reacting a compound of the formula $NC-(CH_2)_n-W-(CH_2)_mCl$, wherein n, m, and W are as defined above for the compound of formula I with a salt of the respective metal or of the halogen-containing moiety to form an intermediate compound and then reacting the intermediate compound with thiourea or a thiourea derivative of the formula

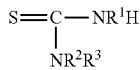

wherein $R^1$, $R^2$ and $R^3$ are as defined above for formula I to afford the a compound of formula I wherein Z is copper, silver, gold, platinum or a halogen-containing moiety selected from $ClO_2$, $BrO_2$, and $IO_2$ wherein the formation of the intermediate and the formation of the acid addition salt are conducted in water or water/alcohol solvent or in a polar solvent, at reflux temperature, and, if desired, preparing the free base or a different acid addition salt. In one embodiment of the invention the solvent is selected from an alcohol selected from methanol, ethanol, isopropanol and mixtures of one or more of the foregoing alcohols with water. The present invention also relates to the preparation of hydrobromide acid addition salts of the compound of formula I and the mesylate salts of the compound of formula I. The hydrobromide acid addition salts are prepared by substituting a bromine containing starting material in the processes described above. The mesylate salts are prepared by substituting a mesylate starting material in the processes described above. A disalt of the present invention may be similarly prepared by using a salt as the starting material. It may be possible to form such a salt if the free base has two basic centers.

DETAILED DESCRIPTION OF THE INVENTION

Figure 1:
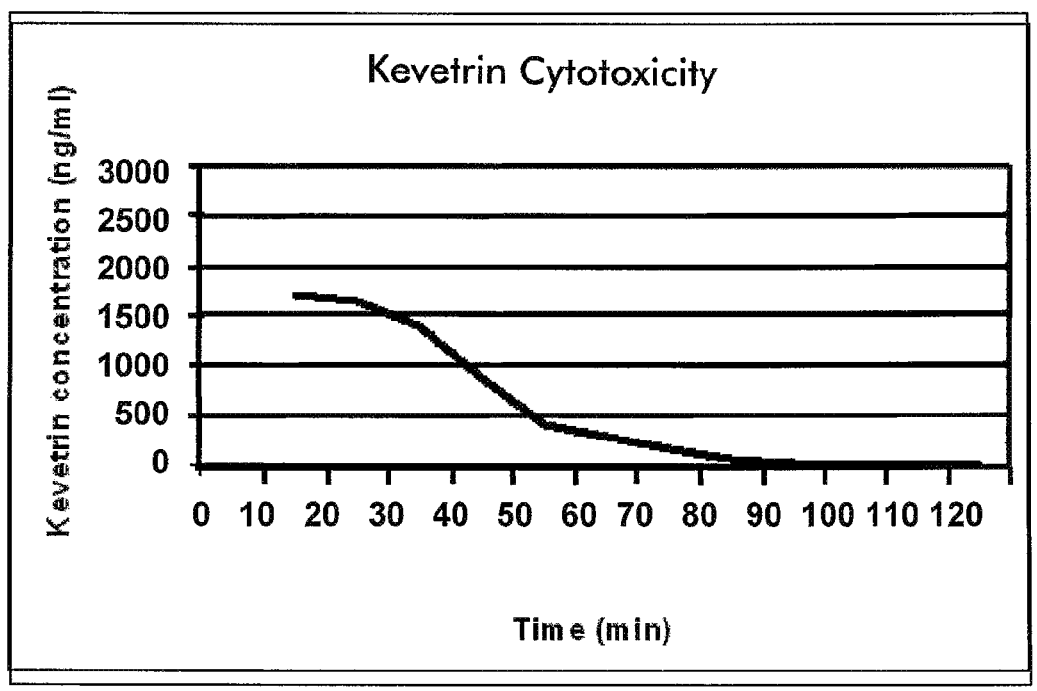
FIG. 1 shows the time dependence of Kevetrin cytotoxicity. Human carcinoma cells were exposed to different concentrations of Kevetrin for 5, 10, 20, 30, or 45 minutes or 1, 2, 6, 24, or 120 hours. Cellular viability expressed as IC50 was plotted verses time of Kevetrin exposure as measured using the MTT assay.

Compounds useful in the present invention wherein Z is sulphur are prepared by reacting thiourea with the appropriate nitrile derivative of the formula $NC-(CH_2)_n-W-(CH_2)_mCl$, wherein n, m, and W are as defined above for the compound of the formula I, in water. Equal amounts of thiourea and a nitrile are added to a 10× volume of water or water/alcohol solvent, or polar solvent, and heated to reflux for about 4 hours at ambient pressure. Non-limiting examples of suitable alcohols for preparing mixtures of water and alcohol or for use as polar solvents include methanol, ethanol and isopropanol. The reaction mixture is allowed to evaporate yielding the desired product. This product is purified by recrystallization from ethanol or another suitable solvent, for example, isopropanol or methanol or mixtures of one of the foregoing alcohols with acetone. The crystalline material is collected by filtration and dried under a high vacuum. Compounds of formula I wherein Z is selected from copper, silver, gold and platinum, or Z is a halogen-containing moiety selected from $ClO_2$, $BrO_2$, and $IO_2$ are similarly prepared.

Compounds of formula I wherein Y in the W moiety is sulphur, oxygen or nitrogen are prepared by selecting the appropriate nitrile derivative wherein sulphur, oxygen or nitrogen is in the desired position on a ring in the W moiety.

One of ordinary skill in the art would know how to select conditions from those discussed above or to make modifications thereto in order to make specific compounds of interest.

Depending on the disease and condition of the patient, the term "treatment" as used herein may include one or more of curative, palliative and prophylactic treatment. The active compounds may be administered, in the treatment of a patient, together with radiation or with other antihyperproliferation compounds such as one or more of cyclophosphamide, cisplatin, carboplatin, Taxol, and Erbitux, as well as other approved antihyperproliferation compounds, in combination or sequentially. Depending on the particular disorder and the condition of the patient, such treatment may be more effective than either compound alone or radiation alone. The precise dosage administered of each active compound for antihyperproliferation, anti-inflammatory, antibacterial or antiviral use will vary depending upon a number of factors, including but not limited to, the type of patient and type of disease state being treated, the age of the patient, and the route(s) of administration.

For administration to human patients, the total daily dose of the active compounds is anticipated to be in the range of 1 mg to 300 mg per kg of body weight, depending on the mode of administration. For example, oral administration may require a total daily dose of from 100 mg to 300 mg per kg of body weight, while an intravenous dose may only require from 20 mg to 200 mg per kg of body weight. The total daily dose may be administered in single or divided doses. For an average human subject having a weight of about 70 kg, the dosage would be about 1400 mg to 21000 mg for oral administration and about 140 mg to 1400 mg for intravenous administration. The physician will readily be able to determine doses for subjects whose weight falls outside this range, such as infants and the elderly. A veterinarian will readily be able to determine doses for other mammals.

In one embodiment, the invention comprises administration of an intravenous solution or suspension comprising 200 mg of an active compound per kg of body weight. For the above-mentioned therapeutic uses, the dosage administered will, of course, vary with the compound employed, the mode of administration, the treatment desired and the disorder indicated. The total daily dose may be administered in single or divided doses. The present invention also encompasses sustained release compositions.

The pharmaceutical composition may, for example, be in a form suitable for oral administration as a tablet, capsule, pill, powder, sustained release formulation, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and an active compound. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Useful components of these compositions include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intrapatient dose-escalation as determined by the skilled artisan. Determining appropriate dosages and regimens for administration of the chemotherapeutic agents are well-known in the relevant art and would be understood to be encompassed by the skilled artisan once provided the teachings disclosed herein.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active compound. The amount of the active compound is generally equal to the dosage of the active compound which would be administered to a subject or a convenient fraction of such a dosage such as, for example, one-half or one-third of such a dosage.

The relative amounts of the active compound, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active compound, a pharmaceutical composition of the invention may further comprise one or more additional therapeutically effective compounds as discussed above.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. Thus, the active compounds may be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous, and kidney dialytic infusion techniques. Suitable devices for such parenteral administration include needle (including microneedle) injectors, needle-free injectors and infusion apparatus.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations as discussed below. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

The active compounds are inhibitors of cellular hyperproliferation or are cell-cycle specific inducers of apoptosis in cancer cells or are both. Therefore, these compounds are useful for treating hyperproliferative diseases and disorders, such as cancer, and are useful for treating diseases and disorders that are responsive to the induction of apoptosis, such as cancer. By having a cell-cycle specific mode of action, these compounds should have a higher therapeutic index compared to standard chemotherapeutic drugs targeting basic cellular processes like DNA replication or interfering with basic cellular molecules like DNA. Thus, for example, the active compounds discussed herein are expected to be useful in targeted cancer therapy. The active compounds may also be effective against angiogenesis.

In the context of this invention, hyperproliferation and analogous terms are used to describe aberrant or disregulated, or aberrant and disregulated, cellular growth, a hallmark of diseases like cancer. Inhibition of cell proliferation and analogous terms are used herein to denote an ability of the compound to retard the growth of and/or kill a cell contacted with that compound as compared to cells not contacted with that compound. Most preferably this inhibition of cell proliferation is 100%, meaning that proliferation of all cells is stopped and/or cells undergo programmed cell death. In some embodiments the contacted cell is a neoplastic cell. A neoplastic cell is defined as a cell with aberrant cell proliferation. A benign neoplasia is described by hyperproliferation of cells, incapable of forming an aggressive, metastasizing tumor in-vivo. In contrast, a malignant neoplasia is described by cells with different cellular and biochemical abnormalities, e.g. capable of forming tumor metastasis. The acquired functional abnormalities of malignant neoplastic cells (also defined as "hallmarks of cancer") are replicative potential ("hyperproliferation"), self-sufficiency in growth signals, insensitivity to anti-growth signals, evasion from apoptosis, sustained angiogenesis and tissue invasion and metastasis.

Inducer of apoptosis and analogous terms are used herein to identify a compound which executes programmed cell death in cells contacted with that compound. Apoptosis is defined by complex biochemical events within the contacted cell, such as the activation of cystein specific proteinases ("caspases") and the fragmentation of chromatin. Induction of apoptosis in cells contacted with the compound might not necessarily be coupled with inhibition of cell proliferation. Preferably, the inhibition of cell proliferation and/or induction of apoptosis is specific to cells with aberrant cell growth (hyperproliferation). Thus, compared to cells with aberrant cell growth, normal proliferating or arrested cells are less sensitive or even insensitive to the proliferation inhibiting or apoptosis inducing activity of the compound. Finally, cytotoxic is used in a more general sense to identify compounds which kill cells by various mechanisms, including the induction of apoptosis/programmed cell death in a cell cycle dependent or cell-cycle independent manner.

Cell cycle specific and analogous terms are used herein to identify a compound as inducing apoptosis only in continuously proliferating cells actively passing a specific phase of the cell cycle, but not in resting, non-dividing cells. Continuously proliferating cells are typical for diseases like cancer and characterized by cells in all phases of the cell division cycle, namely in the G ("gap") 1, S ("DNA synthesis"), G2 and M ("mitosis") phase.

AKT (also known as protein kinase B (PKB)), and its gene family products, has been identified as a serine/threonine protein kinase. Testa et al., Proc. Natl. Acad. Sci., 2001, 98, 10983-10985; Lawlor et al., J. Cell Sci., 2001, 114, 2903-2910; Duan, Circ. Res., 2000, 86, 15-23. PKB plays an important role in cell proliferation, apoptosis and response to insulin. Accordingly, modulation of PKBs is of interest in the treatment of tumorigenesis, abnormal cell proliferation, and diabetes. In the context of this invention, hyperproliferation and analogous terms are used to describe aberrant/disregulated cellular growth, a hallmark of diseases like cancer.

PKB Assay

A kinase assay for evaluating PKB activity comprises active PKB enzymes, a PPKB specific substrate and $P^{33}$-labeled ATP. Two forms of PKBa enzymes are used, the full length PKBα and a kinase domain of PKBα with pleckstrin domain (amino acids 1-117) deleted. Both PKB enzymes are available from Upstate Cell Signaling Solutions (Catalog Numbers 14-276 and 14-341). The PKB substrate used is a synthetic peptide (ARKRERTYSFGHHA) as described in Obata et al., J. Biol. Chem. 2000, 275, 36108-36115. The phosphorylated substrate is captured by a phosphocellulose membrane filter plate (Millipore) and measured by a Wallac Microbeta liquid scintillation counter (Perkin Elmer).

PKB activity in cells is assayed in a PTEN null human breast tumor cell line MDA-MB-468. The phosphorylation status of PKB substrate FKHRL1, GSK3a/b, and Tuberin are measured by immunoassays utilizing phospho-specific antibodies (Cell signaling technology).

The effect of PKB inhibition on cell viability is measured in a range of human tumor cell lines including but not limiting to MDA-MB-468, MDA-MB-231, U87-MG, LN-229, PC-3, DU145. The cells are treated in regular growth media for 72 hours and cell viability is measured by Alamar Blue (Biosource, UK).

The following non-limiting Examples illustrate the preparation of the active compounds.

$^1$H Nuclear magnetic resonance (NMR, Mercury-300) spectra were consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The mass spectra (m/z) were recorded on an Agilent model 1100 mass spectrometer using either electrospray ionisation (ESI) or atmospheric pressure chemical ionisation (APCI). The following abbreviations have been used for common solvents: CDCl$_3$ deuterochloroform; D$_6$-DMSO deuterodimethylsulphoxide; CD$_3$OD deuteromethanol.

EXAMPLE 1

S-(3-cyanopropyl)isothiourea hydrochloride (Also Known as Kevetrin)

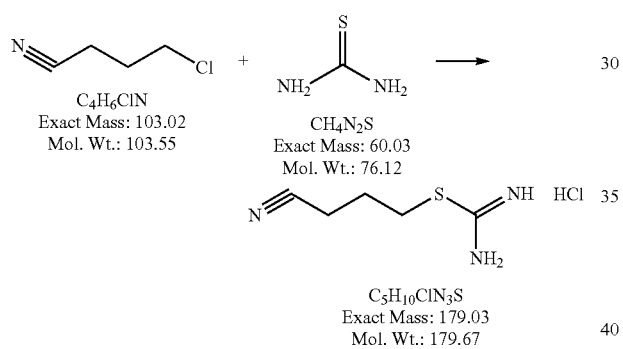

The γ-Chlorobutyronitrile (5.0 g, 48.3 mmol) and thiourea (4.04 g, 53.1 mmol) were mixed in 40 ml of water. The mixture was heated to reflux for 3 to 4 hours. The reaction mixture was evaporated and 20 ml of ethanol was added and then evaporated as well. This was repeated three times. After that, 10 ml of methanol and 30 ml of acetone were added and the mixture was stirred for one hour. The crystalline material was filtered and the product was dried under high vacuum overnight to yield 5.44 g (30.3 mmol, yield 62.7%) of product as white crystals, melting point 134-135° C., with purity greater than 97%. $^1$H NMR (300 MHz, d$_6$DMSO) δ 1.89 (m, 2 H), 2.63 (t, 2H, J=7.2 Hz), 3.23 (t, 2H, J=7.2 Hz), 3.38 (s, 3H).

$^{13}$C NMR (75 MHz) δ 15.3, 25.0, 28.8, 119.8, 169.7.

Formula: C$_5$H$_{10}$ClN$_3$S

Exact Mass: 179.03

Mol. Wt.: 179.67 m/e: 179.03 (100.0%), 181.03 (32.1%), 180.03 (7.4%), 181.02 (4.5%), 182.03 (2.0%), 183.02 (1.5%). C, 33.42; H, 5.61; Cl, 19.73; N, 23.39; S, 17.85

Anal. Calcd: 33.42 5.61 23.39 17.85

Found: 33.44 5.48 23.40 18.31

EXAMPLE 2

S-(2-cyanoethyl)isothiourea hydrochloride

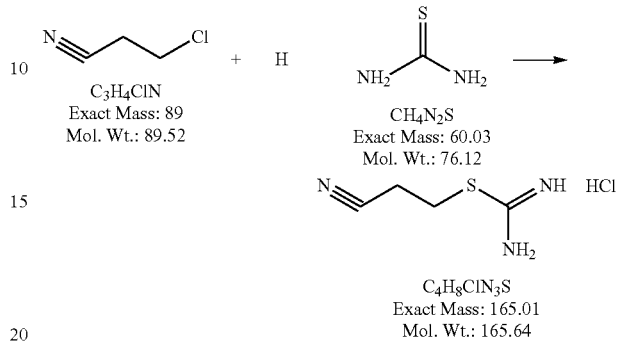

The 3-chloropropanenitrile (4.32 g, 48.3 mmol) and thiourea (4.04 g, 53.1 mmol) are mixed in 40 ml of water. The mixture is heated to reflux for 3 to 4 hours. The reaction mixture is evaporated and 20 ml of ethanol is added and then evaporated as well. This is repeated three times. After that, 10 ml of methanol and 30 ml of acetone are added and the mixture is stirred for one hour. The crystalline material is filtered and the product is dried under high vacuum overnight to obtain S-(2-cyanoethyl)isothiourea hydrochloride.

EXAMPLE 3

S-(4-cyanobutyl)isothiourea hydrochloride

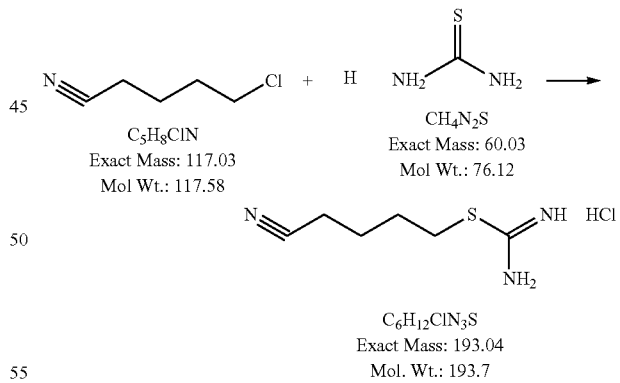

The 5-chloropentanenitrile (5.68 g, 48.3 mmol) and thiourea (4.04 g, 53.1 mmol) are mixed in 40 ml of water. The mixture is heated to reflux for 3 to 4 hours. The reaction mixture is evaporated and 20 ml of ethanol are added and then evaporated as well. This is repeated three times. After that, 10 ml of methanol and 30 ml of acetone are added and the mixture is stirred for one hour. The crystalline material is filtered and the product is dried under high vacuum overnight to yield S-(4-cyanobutyl)isothiourea hydrochloride.

EXAMPLE 4

S-(5-cyanopentyl)isothiourea hydrochloride

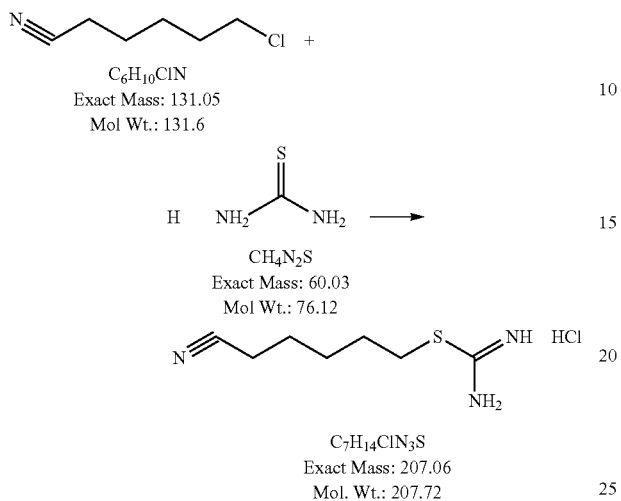

The 6-chlorohexanenitrile (6.36 g, 48.3 mmol) and thiourea (4.04 g, 53.1 mmol) are mixed in 40 ml of water. The mixture is heated to reflux for 3 to 4 hours. The reaction mixture is evaporated and 20 ml of ethanol is added and then evaporated as well. This is repeated three times. After that, 10 ml of methanol and 30 ml of acetone are added and the mixture is stirred for one hour. The crystalline material is filtered and the product is dried under high vacuum overnight to yield S-(5-cyanopentyl)isothiourea hydrochloride.

EXAMPLE 5

S-(4-cyanomethylphenyl)methylisothiourea hydrochloride

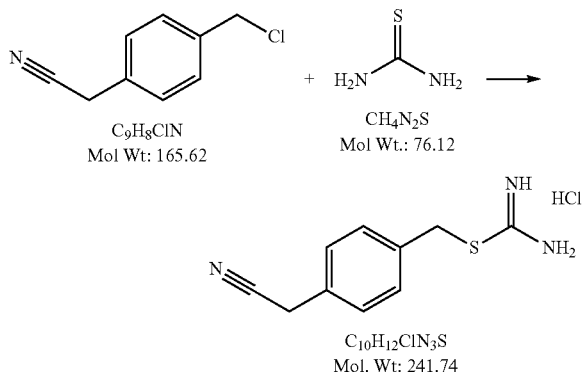

The 4-chloromethylphenylacetonitrile (200 mg, 1.21 mmol) and thiourea (101 mg, 1.33 mmol) were mixed in 1 ml of methanol. The mixture was heated to reflux for 3 to 4 hours. The reaction mixture was evaporated. After that, 1 ml of methanol and 4 ml of acetone were added and the mixture was stirred for one hour. The crystalline material was filtered and the product was dried under high vacuum overnight to yield 219 mg (0.91 mmol, yield 75%) of product as off white crystals, with purity greater than 95%. $^1$H NMR (300 MHz, $d_6$-DMSO) δ 4.03 (s, 2 H), 4.50 (s, 2H), 7.35 (d, 2H, J=8.23 Hz), 7.45 (d, 2H, J=8.23 Hz), 9.22 (s, 4H). (M+H) 206.00

Formula: $C_{10}H_{12}ClN_3S$
Exact Mass: 241.04 (205.07)
Mol. Wt.: 241.74
m/e: 241.04 (100.0%), 243.04 (36.6%), 242.05 (11.0%), 244.04 (4.6%), 242.04 (1.9%), 245.04 (1.5%)

EXAMPLE 6

S-2(4-[(2-cyanoethyl]phenyl)ethylisothiourea mesylate

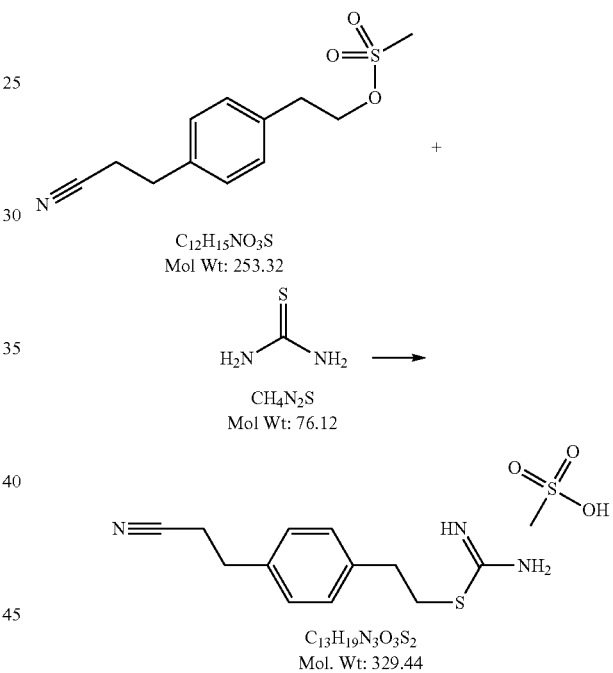

The mesylate (200 mg, 0.79 mmol) and thiourea (66 mg, 0.87 mmol) were mixed in 1 ml of methanol. The mixture was heated to reflux for 3 to 4 hours. The reaction mixture was evaporated. After that, 1 ml of methanol and 4 ml of acetone were added and the mixture was stirred for one hour. The crystalline material was filtered and the product was dried under high vacuum overnight to yield 203 mg (0.62 mmol, yield 78%) of product as off white crystals, with purity greater than 95%. $^1$H NMR (300 MHz, $d_6$-DMSO) δ 2.35 (s, 3H), 2.80 (m, 2H), 2.85 (m, 2H), 2.91 (t, 2H, J=7.4), 3.42 (t, 3H, J=7.4), 7.24 (s, 4H), 9.04 (s, 4H). (M+H) 234.07

Formula: $C_{13}H_{19}N_3O_3S_2$
Exact Mass: 329.09 (233.10)
Mol. Wt.: 329.44
m/e: 329.09 (100.0%), 330.09 (16.0%), 331.08 (9.1%), 331.09 (1.9%), 332.09 (1.4%), 330.08 (1.1%)

EXAMPLE 7

S-(2-cyanomethylphenyl)methylisothiourea hydrochloride

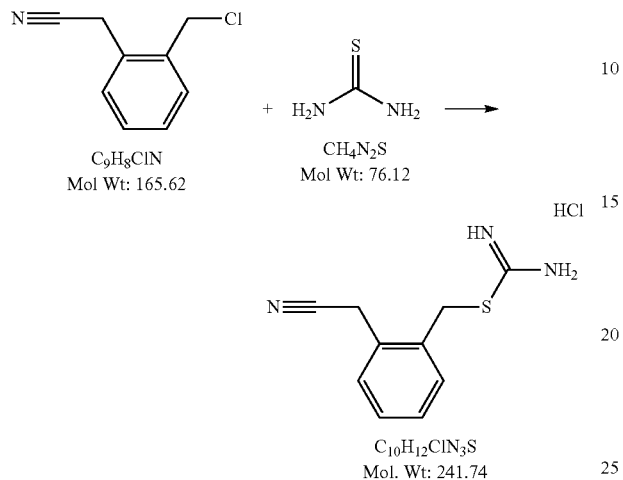

The 2-chlormethylphenylacetonitrile (200 mg, 1.21 mmol) and thiourea (101 mg, 1.33 mmol) were mixed in 1 ml of methanol. The mixture was heated to reflux for 3 to 4 hours. The reaction mixture was evaporated. After that, 1 ml of methanol and 4 ml of acetone were added and the mixture was stirred for one hour. The crystalline material was filtered and the product was dried under high vacuum overnight to yield 231 mg (0.95 mmol, yield 79%) of product as off white crystals, with purity greater than 95%. $^1$H NMR (300 MHz, $d_6$-DMSO) δ 4.14 (s, 2H), 4.56 (s, 2H), 7.37 (m, 2H), 7.45 (m, 2H), 9.23 (s, 4H). (M+H) 205.97

Formula: $C_{10}H_{12}ClN_3S$
Exact Mass: 241.04 (205.07)
Mol. Wt.: 241.74
m/e: 241.04 (100.0%), 243.04 (36.6%), 242.05 (11.0%), 244.04 (4.6%), 242.04 (1.9%), 245.04 (1.5%)

EXAMPLE 8

S-(6-cyanomethylpyridin-2-yl)methylisothiourea hydrochloride

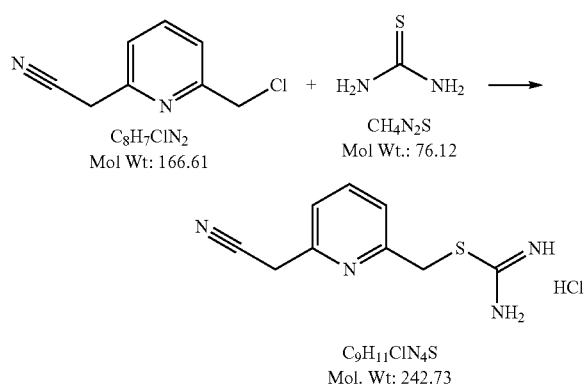

The 6-chloromethyl-2-pyridylacetonitrile (200 mg, 1.20 mmol) and thiourea (101 mg, 1.32 mmol) were mixed in 1 ml of methanol. The mixture was heated to reflux for 3 to 4 hours. The reaction mixture was evaporated. After that, 1 ml of methanol and 4 ml of acetone were added and the mixture was stirred for one hour. The crystalline material was filtered and the product was dried under high vacuum overnight to yield 216 mg (0.89 mmol, yield 74%) of product as off white crystals, with purity greater than 95%. $^1$H NMR (300 MHz, $d_6$-DMSO) δ 4.29 (s, 2H), 4.64 (s, 2H), 7.41 (d, 1H, J=7.78), 7.51 (d, 1H, J=7.78), 7.91 (t, 1H, J=7.78), 9.46 (s, 4H). (M+H) 207.00

Formula: $C_6H_{11}ClN_4S$
Exact Mass: 242.04 (206.06)
Mol. Wt.: 242.73
m/e: 242.04 (100.0%), 244.04 (36.7%), 243.04 (12.0%), 245.04 (3.9%), 246.03 (1.5%)

EXAMPLE 9

S-(3-cyanomethylphenyl)methylisothiourea hydrochloride

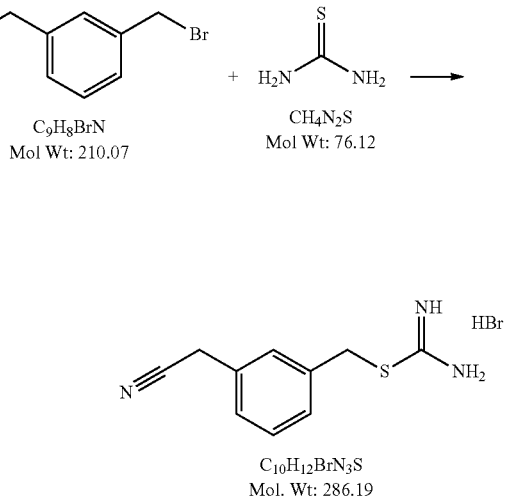

The 3-bromomethylphenylacetonitrile (200 mg, 0.95 mmol) and thiourea (80 mg, 1.05 mmol) were mixed in 1 ml of methanol. The mixture was heated to reflux for 3 to 4 hours. The reaction mixture was evaporated. After that, 1 ml of methanol and 4 ml of acetone were added and the mixture was stirred for one hour. The crystalline material was filtered and the product was dried under high vacuum overnight to yield 215 mg (0.75 mmol, yield 79%) of product as off white crystals, with purity greater than 95%. $^1$H NMR (300 MHz, $d_6$-DMSO) δ 4.08 (s, 2H), 4.53 (s, 2H), 7.31 (m, 2H), 7.40 (m, 2H), 9.25 (s, 4H). (M+H) 206.00

Formula: $C_{10}H_{12}BrN_3S$
Exact Mass: 284.99 (205.07)
Mol. Wt.: 286.19
m/e: 286.99 (100.0%), 284.99 (98.1%), 287.99 (12.7%), 286.00 (10.7%), 288.99 (4.5%), 285.99 (1.9%)

EXAMPLE 10

S-(1-cyanomethylnaphth-2-yl))methylisothiourea hydrochloride

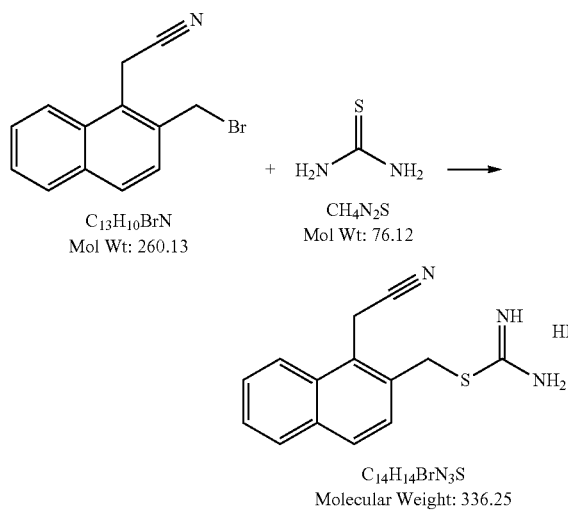

The 2-bromomethyl-1-napthylacetonitrile (200 mg, 0.77 mmol) and thiourea (64 mg, 0.85 mmol) were mixed in 1 ml of methanol. The mixture was heated to reflux for 3 to 4 hours. The reaction mixture was evaporated. After that, 1 ml of methanol and 4 ml of acetone were added and the mixture was stirred for one hour. The crystalline material was filtered and the product was dried under high vacuum overnight to yield 215 mg (0.64 mmol, yield 83%) of product as off white crystals, with purity greater than 95%. $^1$H NMR (300 MHz, $d_6$-DMSO) δ 4.57 (s, 2H), 4.83 (s, 2H), 7.63 (m, 2H), 7.72 (m, 1H), 8.05 (m, 2H), 8.2 (d, 1H, J=8.24), 9.1 (s, 2H), 9.28 (s, 2H). (M+H) 256.00.

Formula: $C_{14}H_{14}BrN_3S$
Exact Mass: 335.01 (255.08)
Mol. Wt.: 336.25
m/e: 335.01 (100.0%), 337.01 (97.6%), 336.01 (17.1%), 338.01 (16.4%), 337.00 (4.5%), 339.00 (4.4%), 339.01 (1.4%), 338.00 (1.1%), 337.02 (1.1%)

EXAMPLE 11

Depicted below are chemical reactions showing the preparation of compounds of the invention. As illustrated, these compounds may be prepared in a manner analogous to that of Example 1 by reacting an appropriate nitrite derivative with thiourea. Thiourea may be replaced by derivatives where one, two or three of the four substituents on the nitrogen atoms are other than hydrogen to provide other compounds of the formula I.

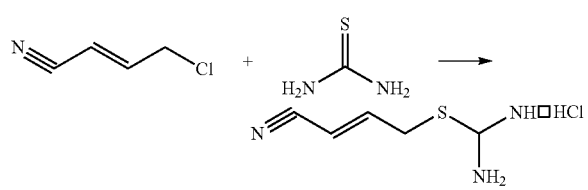

-continued

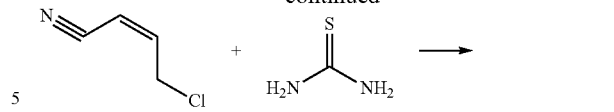

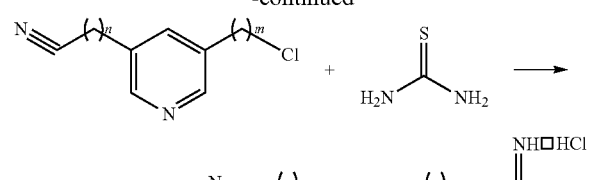
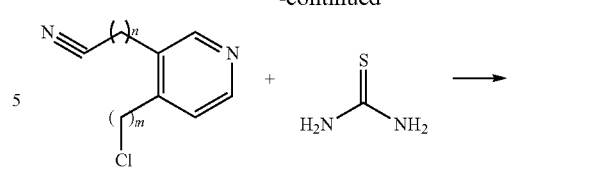
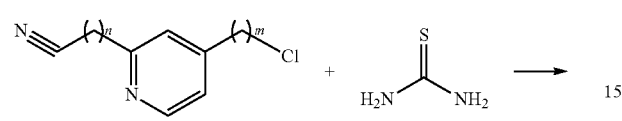
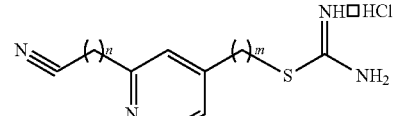
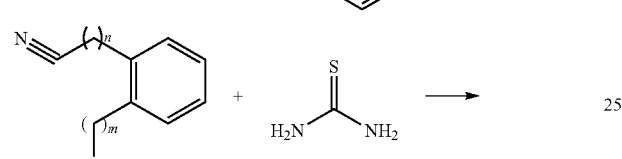
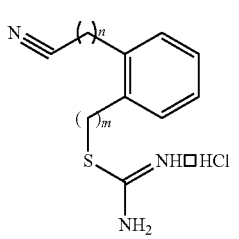
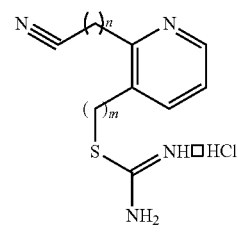
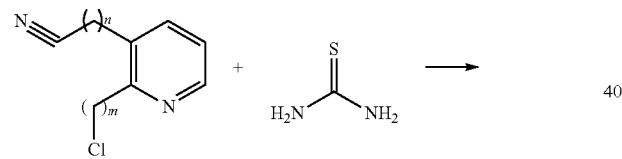
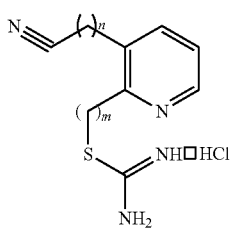
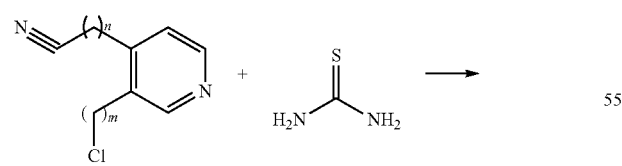
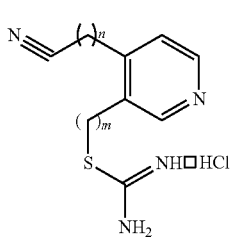
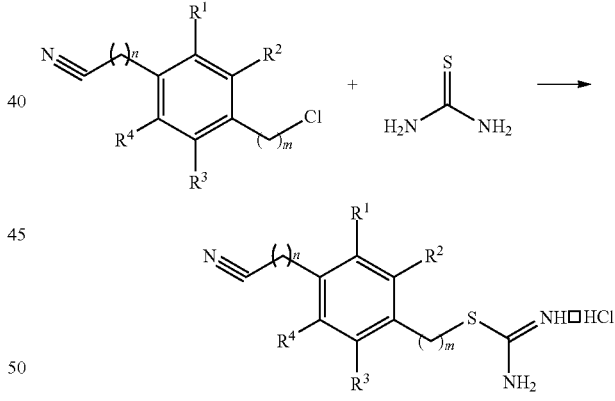
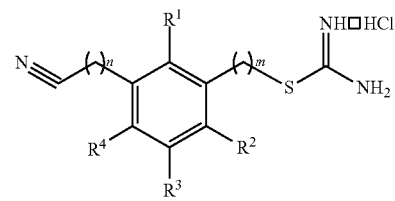

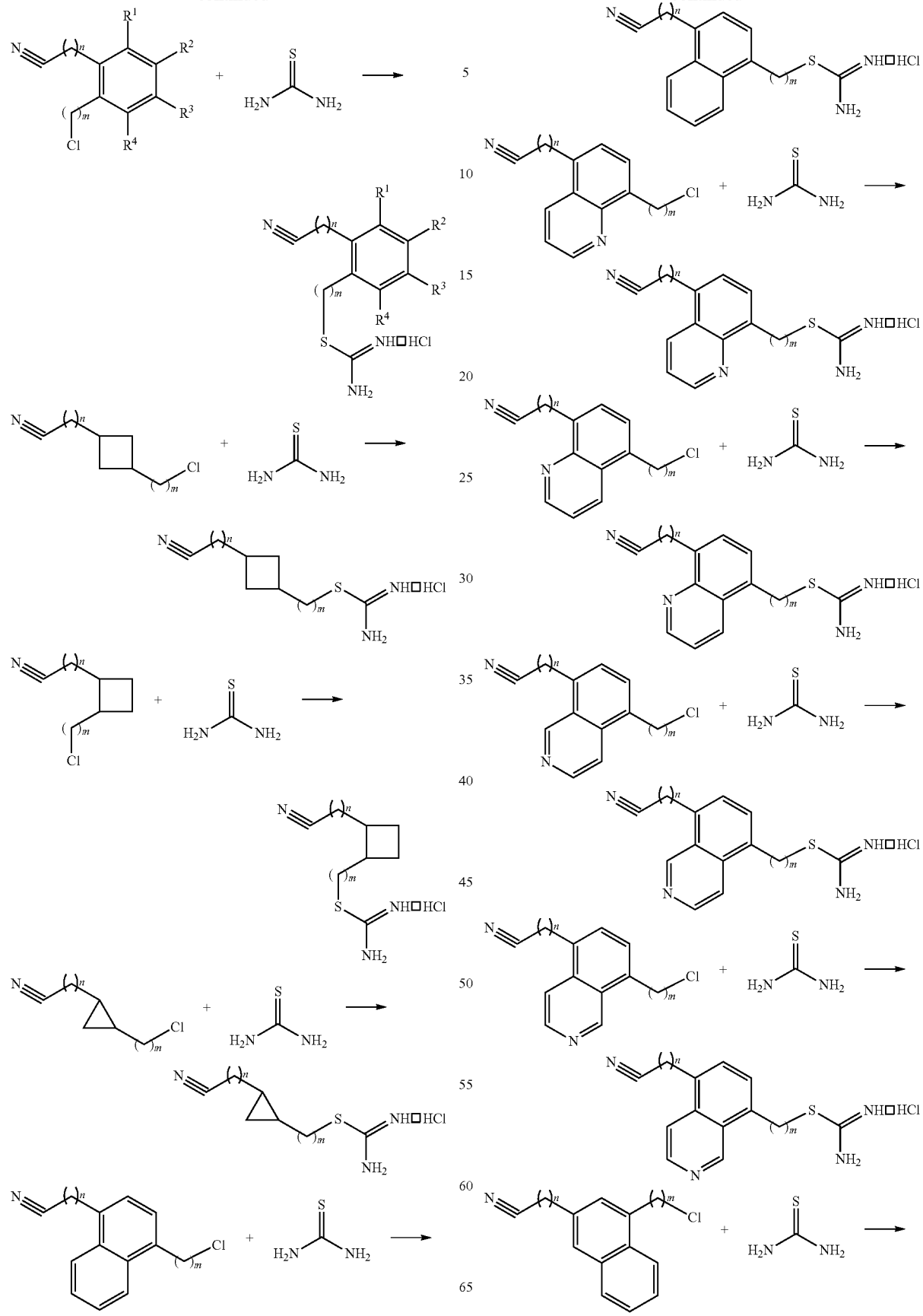

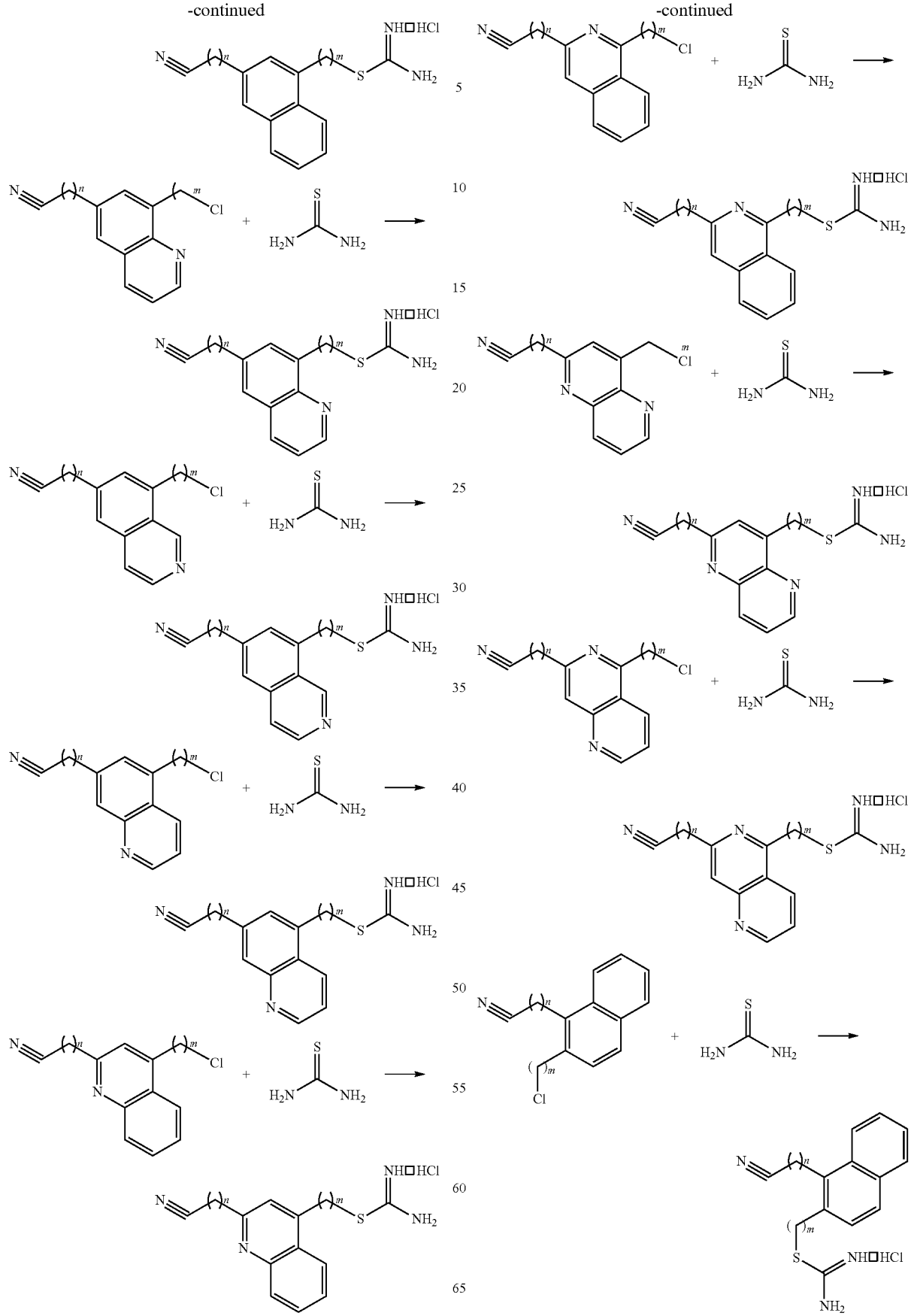

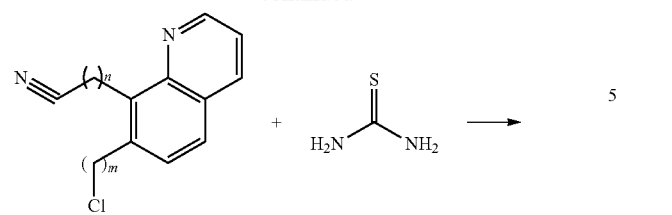
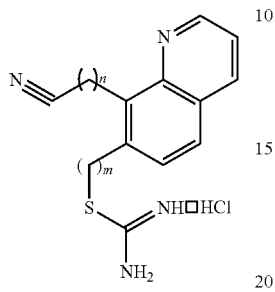
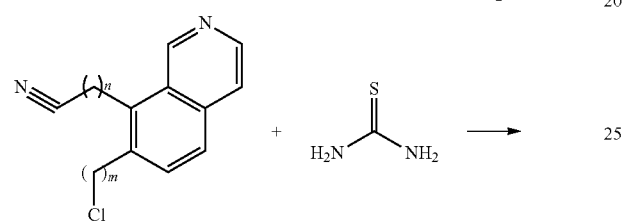
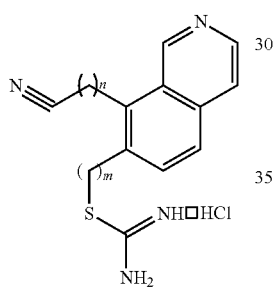
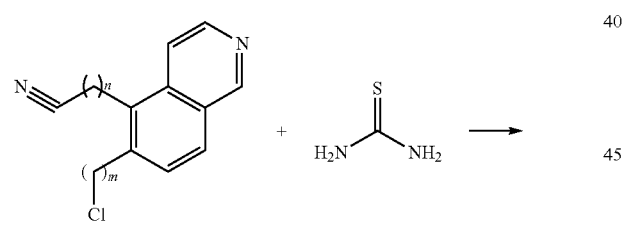
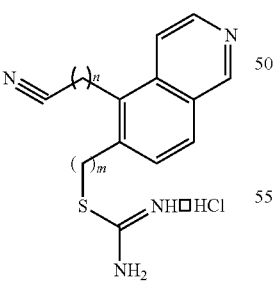
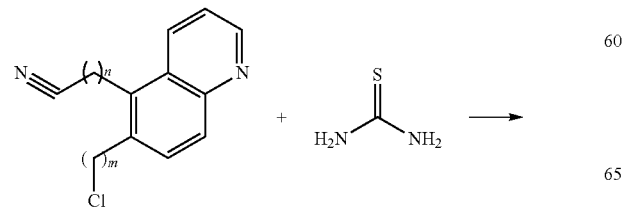
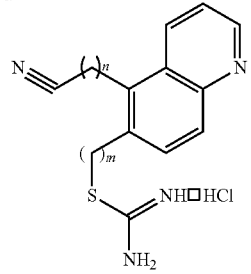
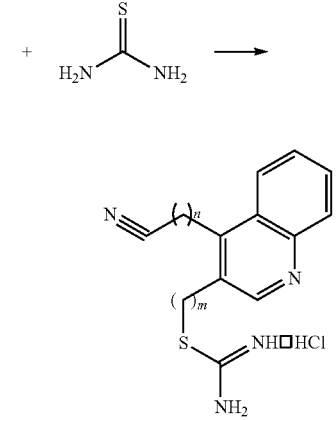
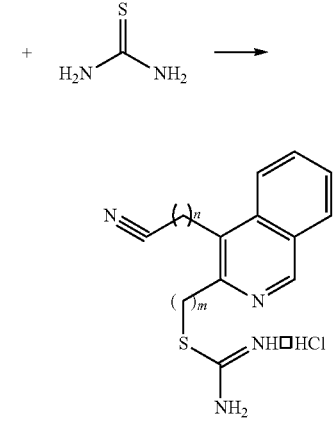
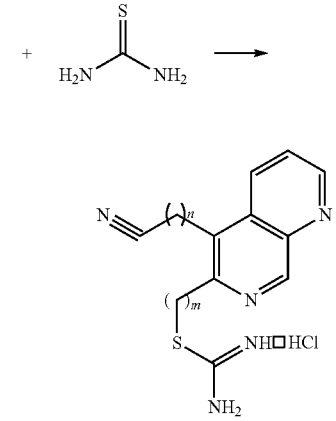

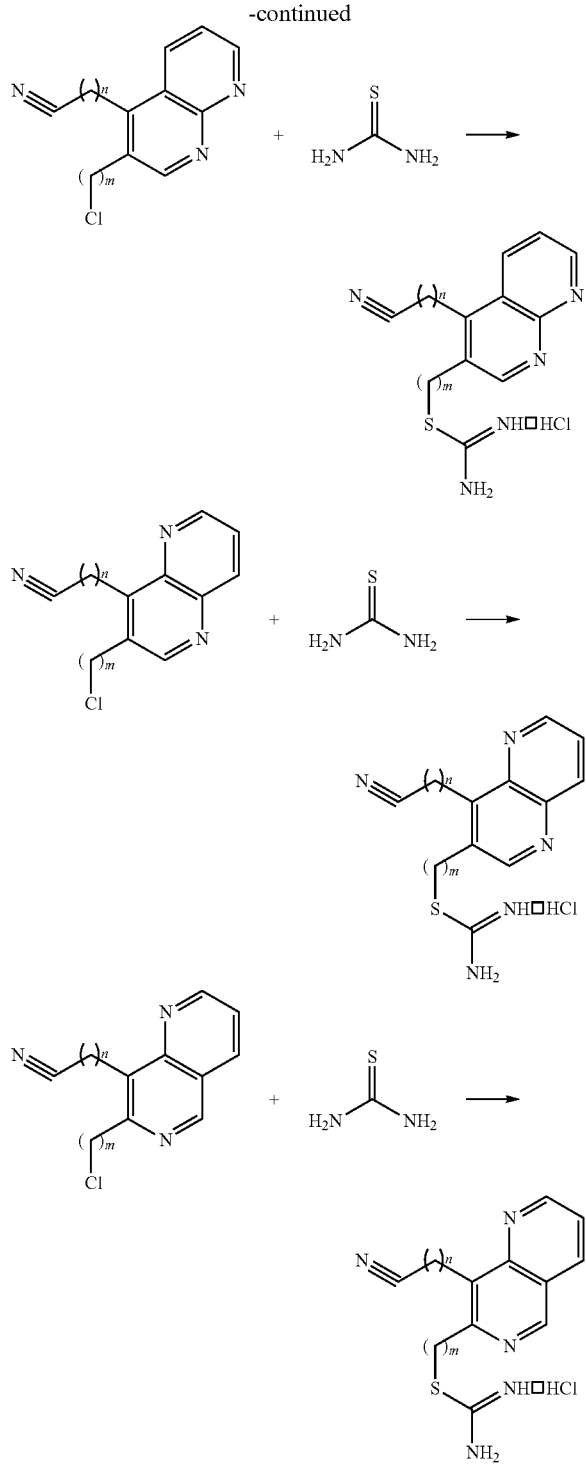

In the reactions depicted in this Example n and m are zero or independently integers from 1 to 8 and $R^1$, $R^2$, $R^3$, and $R^4$ may be, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. $R^1$, $R^2$, $R^3$, and $R^4$ may also be alkenyl and alkynyl. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), and 1-propynyl.

The hydrochloride salts prepared as described above may be converted to the corresponding free base or to other pharmaceutically acceptable salts by known methods. Other pharmaceutically acceptable salts may also be prepared by substituting an appropriate starting material (for example, a bromine containing nitrile, rather than a chlorine containing nitrile) for the nitrile in each of the above reactions.

EXAMPLE 12

Kevetrin Efficacy Studies

Chemicals, Cells and Media

Kevetrin was synthesized as described in Example 1. Cisplatin, Vincristine, 5-FU and Taxol were purchased from Sigma Scientific. H460 and H522 lung carcinoma cells; HT-29, SW-620, and Colo 205, and HCT-15 colon carcinoma cells; OvCar-3, and SKOv-3 ovarian carcinoma cells; DU-145 and PC-3 prostate carcinoma cells; as well as SNB-19 and U-251 glioma cells, HT-1080 fibrosarcoma and SW-480 colon carcinoma cells were purchased from American Type Culture Collection (ATCC) (Rockville, Md.). A2780 ovarian carcinoma cells and their cisplatin-resistant variants A2780/CP1 and A2780/CP2 were generated and characterized in-house. Colon HCT-116 colon carcinoma cells and their p53 –/– and p21 –/– sub-lines were generously provided by Dr. Gangadharan of Central Research Institute, Salem, Ohio whereas HCT-116 supplemented with chromosome 3 was obtained from The Rajiv Gandhi Center for Cancer Research (Rohini, Delhi, India). Except as otherwise indicated, medium and other reagents were purchased from Becton Dickinson. Basal culture medium (RPM-1640) manufactured by Bio Whittaker was sterilized through a 0.22 μm Millex-GV filter unit (Millipore). The prepared medium was stored in small aliquots at 5° C. in the dark. The basal culture medium was supplemented with 10% fetal calf serum (FCS-heat inactivated at 560 C for 30 minutes) for its use as culture medium and mitogen, i.e., Lipopolysaccharide (LPS; 10-50 μg/mL), was added to proliferate the cells.

Growth Inhibition Assays

The cytotoxicity was determined by the Maximum Tolerated Titer (MTT) assay. Briefly, cells were seeded in 24-well tissue culture plates at 10,000-15,000 cells/well and incubated overnight. The exponentially growing cells were then exposed to different drug concentrations for three to four generation times. Cellular viability was determined by exposing cells to the MTT tetrazolium salt for 4 hours at 37° C., and the formation of Formazan was measured at 560 nm by a microplate reader. The concentration inhibiting cell growth by 50% compared with untreated controls was determined from the curves plotting survival as a function of dose. All values are the average of at least three independent experiments each done in duplicates.

Cell Proliferation Assay

MTT solution (10 μL) was added to all wells of 48 hour cultured lymphocytes and incubated for 4 hours at 37° C. Two sets of cultures were prepared; LPS was added to one set only. During this period, Formazan crystals formed at the bottom of each well. Spent media along with suspension of cultured cells was removed by pipetting. Then acidified isopropanol (100 μL of 0.1 N HCl in anhydrous isopropanol) was added to all wells and mixed thoroughly to dissolve the dark blue crystals. After a few minutes at room temperature, plates were read using a plate analyzer with a dual wavelength measuring system: test wavelength of 540 nm, reference wavelength of 630 nm. Plates were read within 1 hour of adding the acidified isopropanol. Cell proliferation was calculated as a stimulation index:

$$\text{Stimulation index} = \frac{A540 \text{ nm with } LPS}{A540 \text{ nm without } LPS}$$

Where A 540=Absorbance at 540 nm.

Immunolocalization of p53

To determine the localization of p53, a protein that causes proliferation of cells, immunocytochemistry was carried out. Briefly, HCT-116 cells (ATCC) were attached to glass slides overnight and exposed to isotoxic concentrations of Kevetrin (300 ng/ml), or cisplatin (11 µg/ml) for 6 hours. After drug exposure, cells were fixed with 3.7% formaldehyde, permeabilized with 0.25% Triton X-100, and blocked with 1% BSA (Bovine Serum Albumin). Cells were then incubated for 1 hour with anti-p53 polyclonal antibodies (Sc-6243; Santa Cruz Biotechnology, California) followed by secondary anti-rabbit FITC-conjugated antibodies (Amersham Life Sciences, U.K.). Coverslips were mounted in Vectashield (Vector Laboratories Vector, U.K.) and analyzed with an epifluorescence microscope Axiovert 100M equipped with appropriate filters and laser confocal scanning system LSM 510 by using a plan Apochromat x63 objective (Zeiss).

Western Blot Analysis

Western blot analysis was performed. Whole cell lysates were prepared from cells treated with isotoxic concentrations of Kevitren (300 ng/ml), or cisplatin (11 µg/ml) for 6 hours. Proteins (50 µg/lane) were separated on a 4-12% polyacrylamide SDS gel and transferred to PolyScreen membranes (Millipore, Bedford, Mass.). The presence of p53, p21, and α-actin was revealed by anti-p53 antibodies (Sc-6243; Santa Cruz Biotechnology), anti-p21 antibodies (Sc-3976; Santa Cruz Biotechnology), and anti-actin antibodies (Sc-1616; Santa Cruz Biotechnology), respectively, followed by incubation with peroxidase-conjugated secondary antibodies (Jackson ImmunoResearch, West Grove, Pa.) and detection by enhanced chemiluminescence (New England Nuclear, Hebron, Conn.).

Influence of Kevetrin on the Viability of Human Tumor Cell Lines

The influence of Kevetrin on the viability of 10 different types of human tumor cells, including carcinomas of the lung, colon, breast, ovary, prostate, sarcomas, gliomas, and leukemias, was determined using the Cell Proliferation Assay described above. Cellular viability was measured after continuous exposure to Kevetrin for three doubling times. The indicated concentrations of Kevetrin correspond to the average $IC_{50}s$. The results are set forth below. Generally. Kevetrin has potent activity toward human tumor cells of epithelial origin. The cytotoxic effect of Kevetrin was most pronounced toward non-small cell lung, colon and ovarian carcinomas with $IC_{50}s$ ranging from 11 to 68 ng/ml. Interestingly. Kevetrin also showed potent activity toward malignant glioma cells ($IC_{50}s$ ~30 ng/ml).

Cytotoxicity of Kevetrin of 10 Different Human Tumor Cell Lines

| Cell type | Cell Line | $IC_{50}$ Concentration |
| --- | --- | --- |
| colon carcinoma | Colo 205 | 6 µg/ml |
| squamous cell carcinoma | SCC 15 | 12 µg/ml |
| colon carcinoma | HCT-116 | 21 µg/ml |
| colon carcinoma | HT-29 | 29 µg/ml |
| prostate carcinoma | LnCap | 52 µg/ml |
| ovarian carcinoma | SKOV-3 | 58 µg/ml |
| colon carcinoma | SW-480 | 62 µg/ml |
| prostate carcinoma | DU-145 | 64 µg/ml |
| squamous cell carcinoma | SCC-61 | 64 µg/ml |
| Breast carcinoma | MCF-7 | 68 µg/ml |

Time Dependence of Kevetrin Cytotoxicity

To determine the influence of exposure time on the cytotoxic effects of Kevetrin, DU-145, HCT-116, or HT-29 carcinoma cells were exposed to different concentrations of Kevetrin for 5, 10, 20, 30, or 45 minutes or 1, 2, 6, 24, or 120 hours. Clear time-dependent cytotoxic effects of Kevetrin were observed for all three cell lines with longer exposure times being associated with increased cytotoxicity. The results are shown in FIG. 1. The time dependence was particularly dramatic for exposure times ≤30-45 minutes. In contrast, extending the drug exposure time beyond 24 hours had no influence on the cytotoxicity.

Activity Spectra for Kevetrin and Cisplatin

Figure 2:
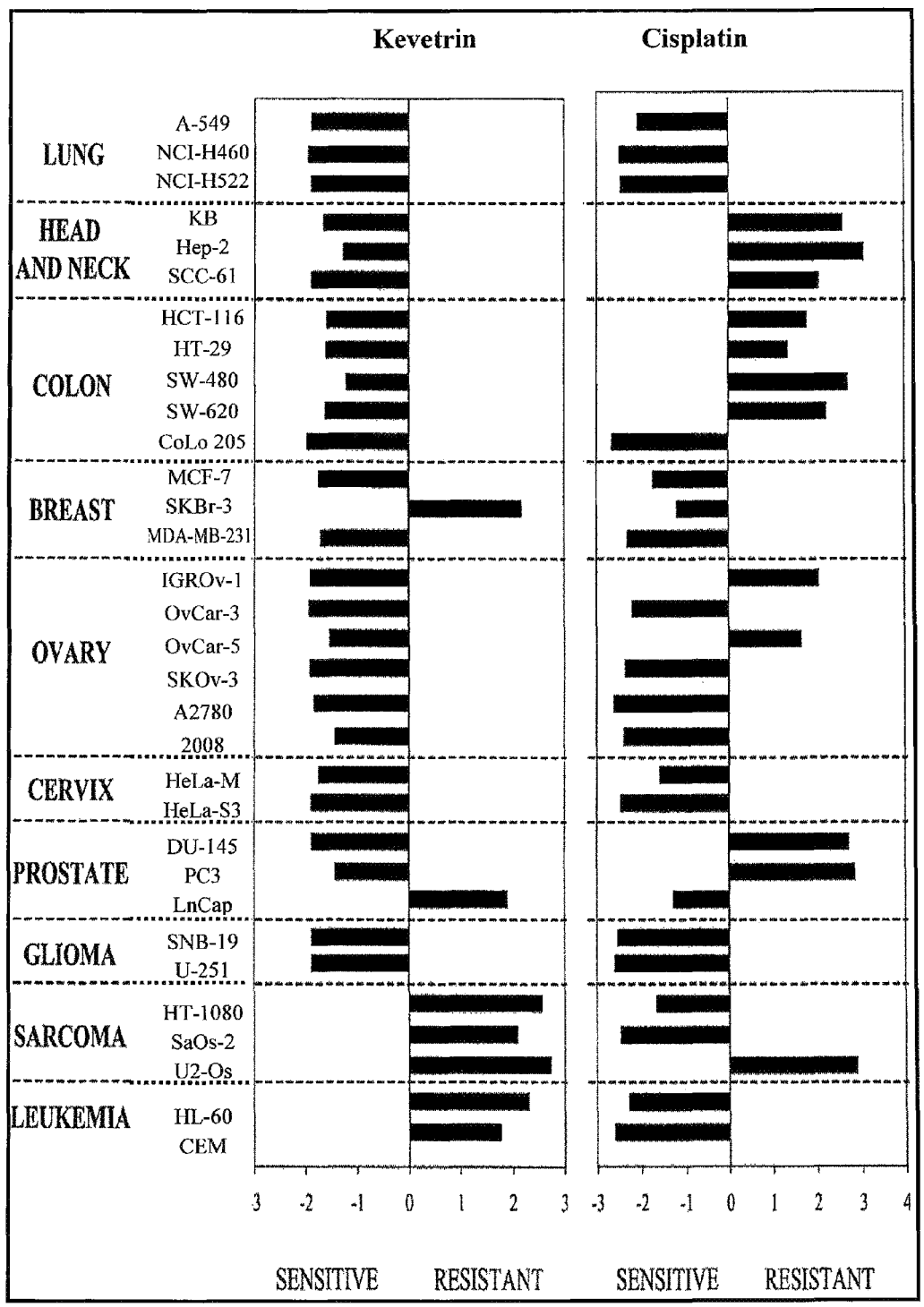
FIG. 2 shows activity spectra for Kevetrin and Cisplatin. The influence of Kevetrin and cisplatin on the viability of the indicated tumor cell lines was measured using the MTT assay after continuous exposure to Kevetrin for three doubling times. The indicated values are calculated as follows: log ($IC_{50}$ individual cell line–$IC_{50}$ average). Negative values indicate that the cell line is more sensitive than the average, whereas positive values indicate that the cell line is more resistant than the average. The average $IC_{50}$s for all cell lines tested were $4.9 \times 10^{-7}$ M for Kevetrin, and $2.1 \times 10^{-6}$ M for cisplatin.

The influence of Kevetrin and cisplatin on the viability of the indicated tumor cell lines was measured using the MTT assay after continuous exposure to Kevetrin for three doubling times and the results are shown in FIG. 2. The indicated values are calculated as follows: $\log(IC_{50}$ individual cell line–$IC_{50}$ average). Negative values indicate that the cell line is more sensitive than the average, whereas positive values indicate that the cell line is more resistant than the average. The average $IC_{50}s$ for all cell lines tested were $4.9 \times 10^{-7}$ M for Kevetrin, and $2.1 \times 10^{-6}$ M for cisplatin. Considering the MTT assay results, comparison of the activity spectra of cisplatin and Kevetrin toward 10 different types of human tumor cells in FIG. 2 shows clear differences between the two drugs. The activity of Kevetrin was more marked than that of cisplatin toward lung, head and neck, breast, ovary, and colon cell lines. Interestingly, Kevetrin showed activity toward all head and neck, non-small cell lung, ovary, colon, and glioma cell lines tested in contrast to cisplatin, which generally exhibited a more heterogeneous response within a given tumor cell type. The difference between Kevetrin and the cisplatin was particularly striking for the three head and neck cancer cell lines, where Kevetrin showed activity toward all of the cell lines, whereas cisplatin was active toward one of the three cell lines. Surprisingly, Kevetrin had comparatively limited activity toward leukemias, which are sensitive to alkylating agents different from what was observed for cisplatin.

In Vivo Efficacy Studies of Kevetrin in Nude Mice Bearing Human Tumor Xenografts Animals and Animal Care The mice were kept on a 12 hour light/12 hour dark cycle with the room temperature being 18-26° C. and a relative humidity of 30-70%. The food and water of the animals was given ad libitum. During this acclimation period, each animal was observed at least once daily for any abnormalities or for the development of infectious disease. Only animals that were determined to be suitable for use were assigned to this study. Any animals considered unacceptable for use in this study were replaced with animals of similar age and weight from the same vendor. When the tumor mass reached, on average, around 100 mm³, the mice were randomized and grouped according to tumor size.

Human Tumor Cell Lines

MDA-MB-231 human breast carcinoma (HTB-26), HT-29 colon carcinoma (HTB-38), PC-3 prostate carcinoma (CRL-1435), HCT-15 P-glycoprotein resistant colon carcinoma were purchased from American Type Culture Collection (Rockville, Md.).

The MDA-MB-231 cell line was originally isolated from the pleural effusion a 51 year old Caucasian female with breast adenocarcinoma. These cells appear to be morphologically epithelial in nature.

The HT-29 cell line was originally isolated in 1964 from a 44 year old Caucasian female with colorectal adenocarcinoma. These cells appear to be morphologically epithelial in nature.

The PC-3 cell line was originally isolated from bone metastasis from a 62 year old Caucasian male with grade IV metastatic prostate adenocarcinoma. These cells exhibit low acid phosphatase and testosterone-5-alpha reductase activities and appear to be morphologically epithelial in nature.

The HCT-15 parental cell line was originally isolated from a male with Dukes' type C colorectal adenocarcinoma. These cells appear to be morphologically epithelial in nature.

The A549 and NCI-H1975 multi-drug resistant human lung carcinoma lines were a gift from the Dana Farber Cancer Institute, Boston, Mass.

Test System

The cells were cultured in 10% FBS RPMI medium. The cells were obtained at passage 5 for further expansion for this efficacy study. Nude mice (Nu/Nu), both male (20 to 24 g) and female (19 to 22 g), were purchased at 6 to 8 weeks old from Charles River Laboratories. These mice were naïve at the beginning of the study and were identified by ear punching. The mice were left for five days to become acclimated to their new environment. Mice were implanted with human tumor cells in a 50:50 mix of RPMI:Matrigel subcutaneously in the right flank of each mouse. Dosing began when tumors reached an average volume of 100 mm³.

In Life Observations and Measurements

The mice were observed daily for any adverse affects. Mice body weights were taken prior to treatment and every other day during and post treatment. If an animal became unwell, any treatment of that animal was suspended. If there was no recovery, the animal was sacrificed. Any animal demonstrating more than 15% weight loss was considered unwell. Any animal that demonstrated a weight loss greater than 20% was sacrificed. Any animals exhibiting sustained ulceration of the skin over the tumor site were sacrificed. Mice tumor size measurements were taken prior to treatment and every other day during and post treatment. The same scientist was responsible for taking the tumor measurements throughout the study.

Terminal Procedures

Once tumors from the vehicle group reached 1000 mm³ all animals from all the groups were sacrificed by $CO_2$ asphyxiation. Upon sacrifice, tumors were removed and weighed.

Study Schedule

Nude mice were implanted with $5 \times 10^6$ tumor cells in a 50:50 mix of RPMI:Matrigel subcutaneously in the right flank of each mouse. Dosing began when tumors reached an average volume of 100 mm³, usually reached by day 14 post implant, and was carried out for 8 days. A necropsy was performed 41 days after treatment ended.

Materials

Kevetrin was prepared as described in Example 1. It was stored at ambient temperature (or $\leq -20°$ C.) and protected from light. For administration to test animals, Kevetrin was suspended in Phosphate Buffered Saline (PBS) (sterile, at pH=7.4). Prior to use, the PBS was stored at ambient temperature. After each suspension was prepared, it was stored at $\leq -20°$ C. and protected from light.

Dosing

The dosing procedure began the day the mice were randomized and grouped. The dose was administered, as discussed in the following paragraph, on days 7, 9 and 11 following tumor implantation. Each dose was administered via the tail vein.

Weight Loss Due to Kevetrin

Figure 3:
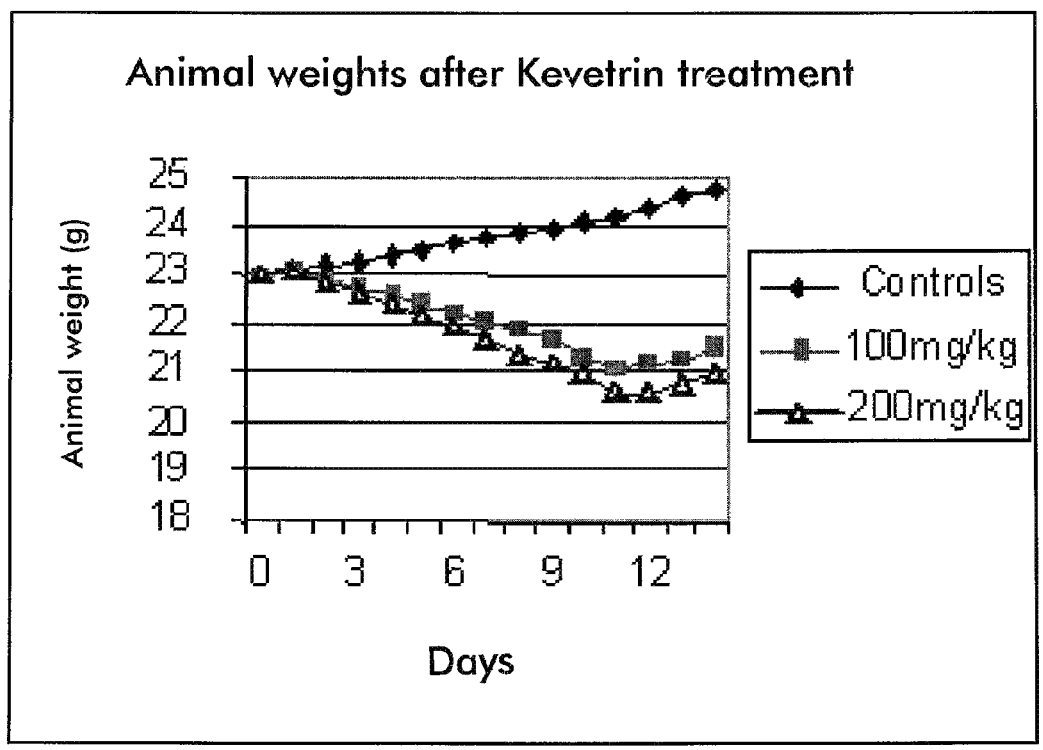
FIG. 3 shows the weight changes of mice due to Kevetrin. Animal weights of mice following treatment with either 100 or 200 mg/kg Kevetrin IV on Day 0 are shown.

When Kevetrin was administered intravenously (IV) to animals bearing tumors, the weight loss due to the administration of the compound was within acceptable limits. 100 mg/kg administered intravenously on days 7, 9, and 11 resulted in a weight loss of 6.8% of the body weight and 200 mg/kg on the same schedule resulted in a weight loss of 9.3%. Both these concentrations may be used to establish the efficacy of Kevetrin. These results are depicted in FIG. 3.

Figure 4:
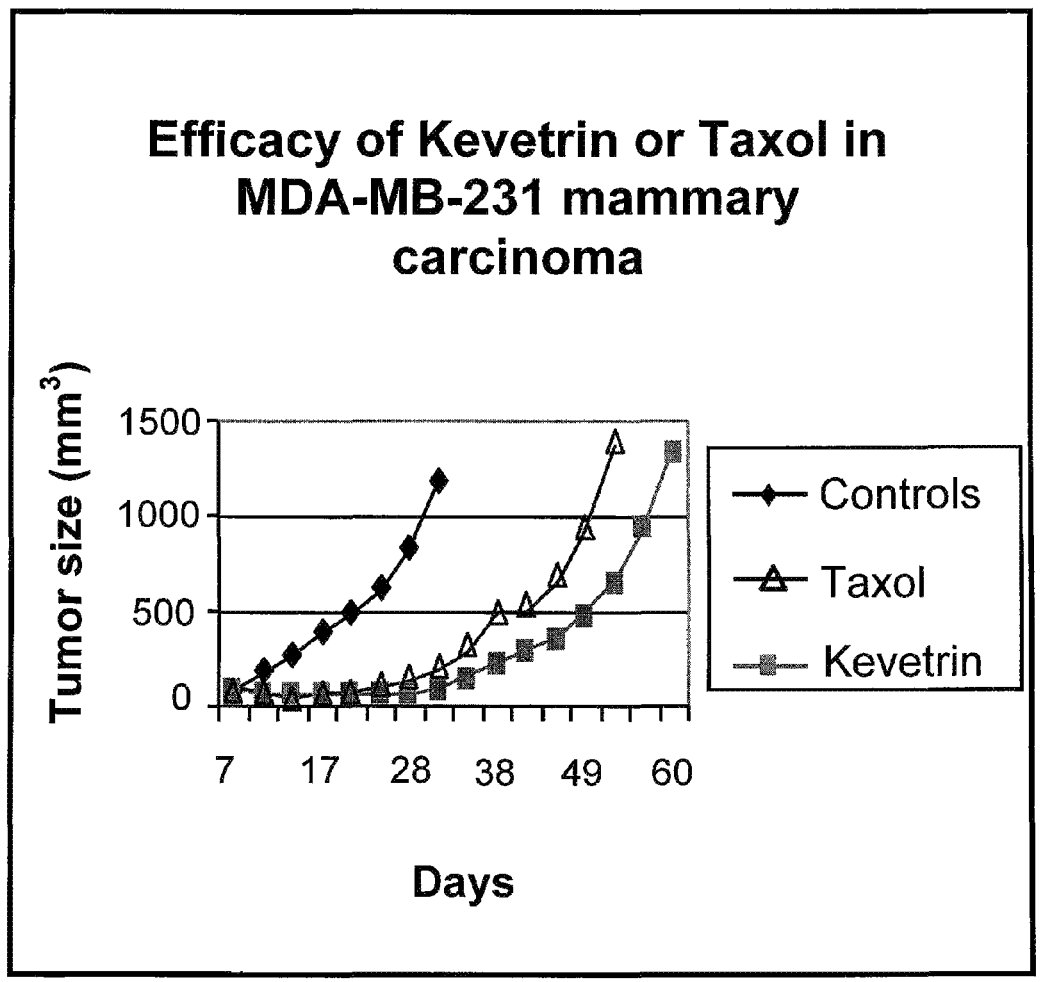
FIG. 4 shows the efficacy of Kevetrin or Taxol in mammary carcinoma. MDA-MB-231 human breast carcinoma bearing mice were treated with 200 mg/kg Kevetrin IV days 7, 9, and 11 compared to 22 mg/kg Taxol IV Days 7, 9, 11 and 13.

Efficacy of 200 mg/kg Kevetrin IV Days 7, 9, & 11 Compared to 22 mg/kg Taxol IV Days 7, 9, 11 & 13 in MDA-MB-231 Human Breast Carcinoma The animals were implanted subcutaneously with human breast carcinoma MDA-MB-231, and the compounds were injected IV as per the schedule. Kevetrin administered animals showed greater efficacy than the Taxol treated animals. The tumor growth was delayed 12 days more than the Taxol treated animals and 32 days more than the untreated control. The results are depicted in FIG. 4.

Efficacy of 200 mg/kg Kevetrin IV Days 7, 9, & 11 Compared to 5-FU Days 7 to 12 in HT-29 Colon Carcinoma.

Figure 5:
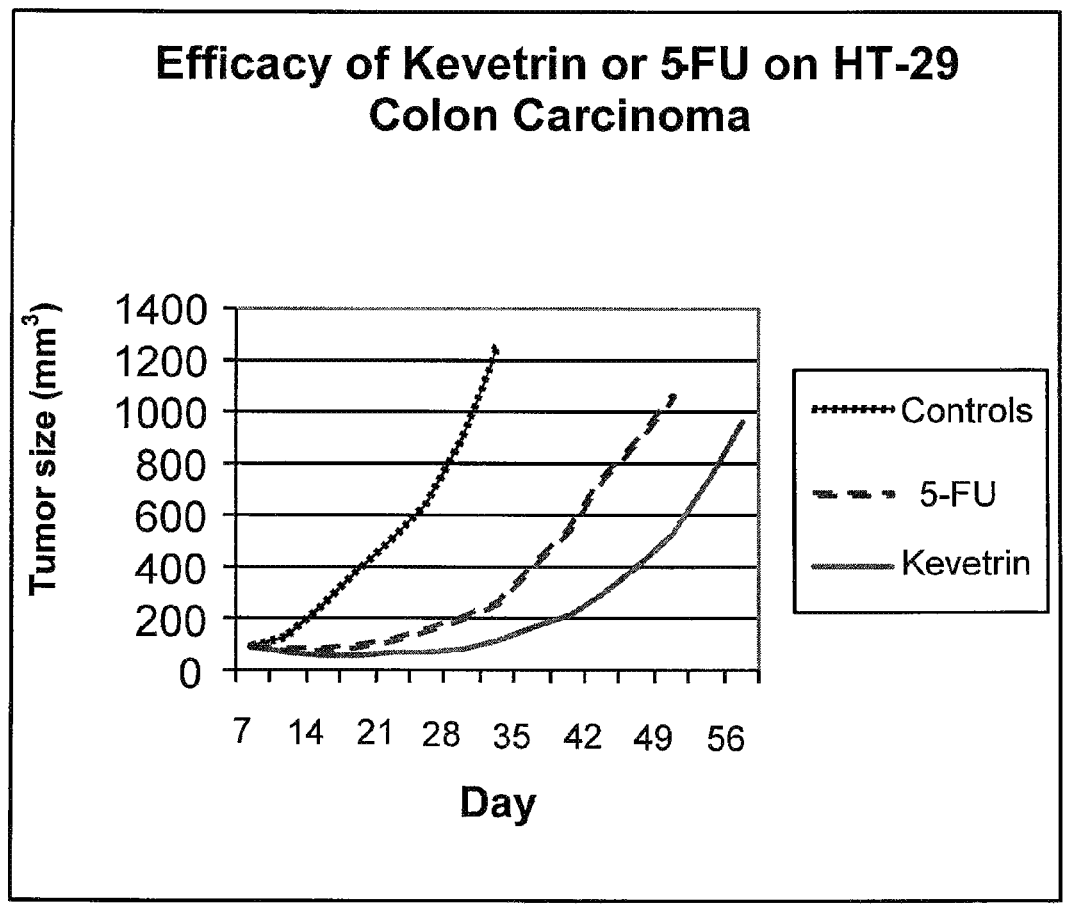
FIG. 5 shows the efficacy of Kevetrin or 5-FU in colon carcinoma. HT-29 tumor bearing nude mice were treated with either 200 mg/kg Kevetrin IV or 5-FU on Days 7, 9, and 11.

The animals were implanted subcutaneously with human colon carcinoma HT-29, and the compounds were injected IV as per the schedule. Kevetrin administered animals showed greater efficacy than the 5-FU treated animals. The tumor growth was delayed 10 days more than the 5-FU treated animals and 33 days more than the untreated control. The results are depicted in FIG. 5.

Figure 6:
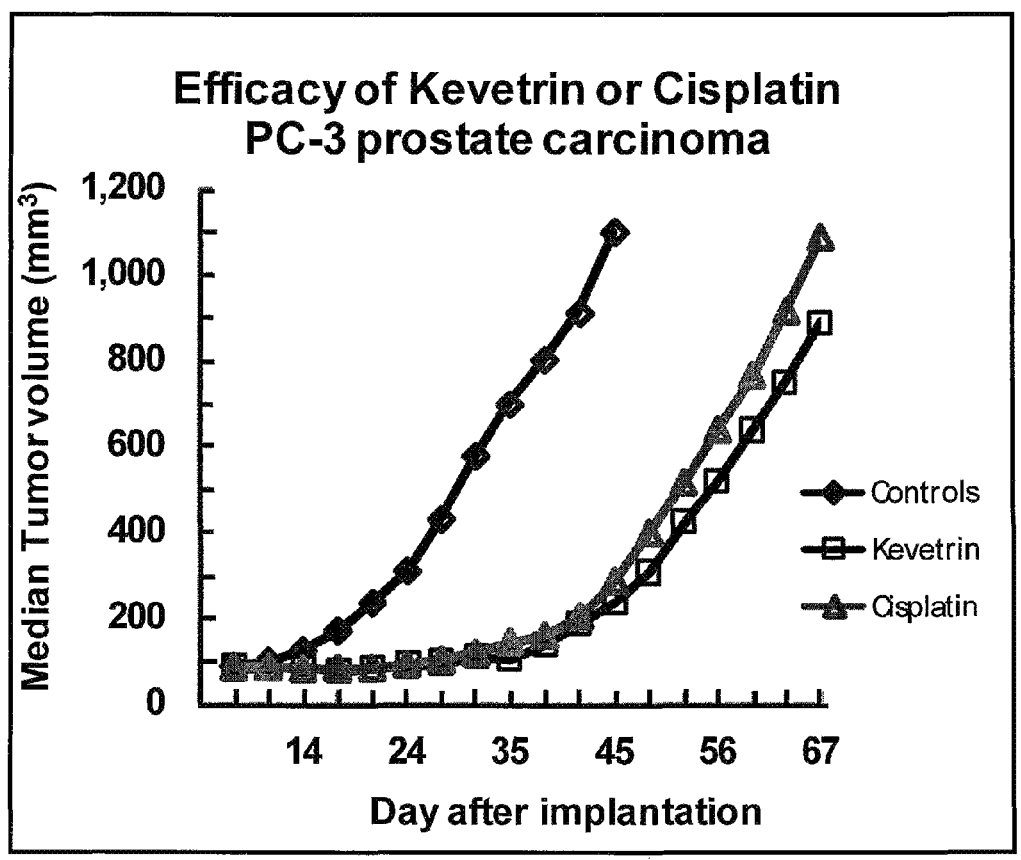
FIG. 6 shows the efficacy of Kevetrin or cisplatin in prostate cancer. PC-3 tumor bearing nude mice were treated with either 200 mg/kg Kevetrin IV on Days 7, 9, 11 or 10 mg/kg cisplatin on Day 7.

Efficacy of 200 mg/kg Kevetrin IV Days 7, 9, & 11 Against 10 mg/kg Cisplatin at on Day 7 in PC-3 Human Prostate Cancer The animals were implanted subcutaneously with human prostate carcinoma PC-3. Kevetrin was injected IV and Cisplatin intraperitoneally (IP) as per the schedule. Kevetrin administered animals showed greater efficacy than the Cisplatin treated animals. The tumor growth was delayed 8 days more than the Cisplatin treated animals and 34 days more than the untreated control. The results are depicted in FIG. 6.

Efficacy of Kevetrin 200 mg/kg Days 7, 9, & 11 Against Taxol at 22 mg/kg on Days 7, 9, 11 & 13 in HCT-15 Human Colon Carcinoma with P-glycoprotein Mediated Resistance.

Figure 7:
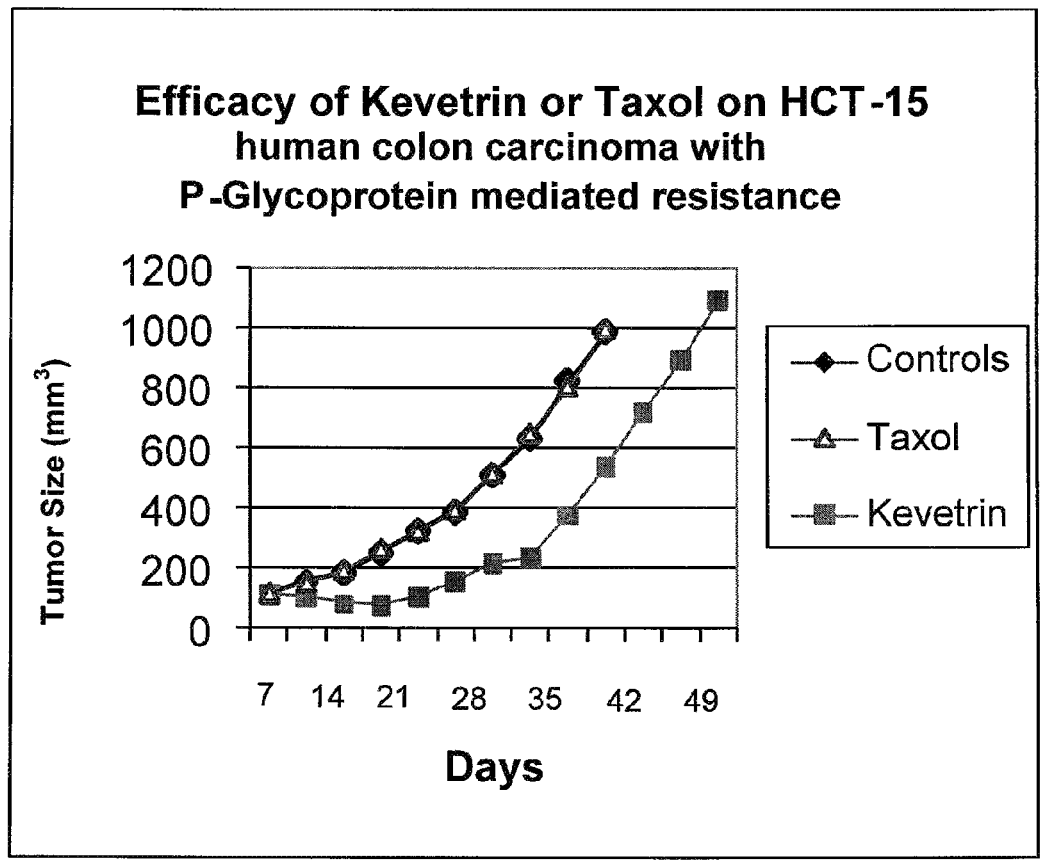
FIG. 7 shows the efficacy of Kevetrin or Taxol in human P-glycoprotein mediated resistant colon carcinoma. HCT-15 tumor bearing nude mice were treated with either 200 mg/kg Kevetrin IV on Days 7, 9, 11 or 22 mg/kg Taxol on Days 7, 9, 11 and 13 post tumor.

The animals were implanted subcutaneously with human colon carcinoma HCT-15, a β-glycoprotein resistant cell model and the compounds were injected IV as per the schedule. Taxol had little effect on such cancer, whereas Kevetrin administered animals showed efficacy in the animals. The tumor growth was delayed 15 days more than the Taxol treated and the untreated control. The results are depicted in FIG. 7.

Efficacy of Kevetrin 200 mg/kg Days 7, 9, & 11 Against Taxol at 22 mg/kg on Days 7, 9, 11 & 13 in A549 Multi-Drug Resistant Human Lung Carcinoma.

Figure 8:
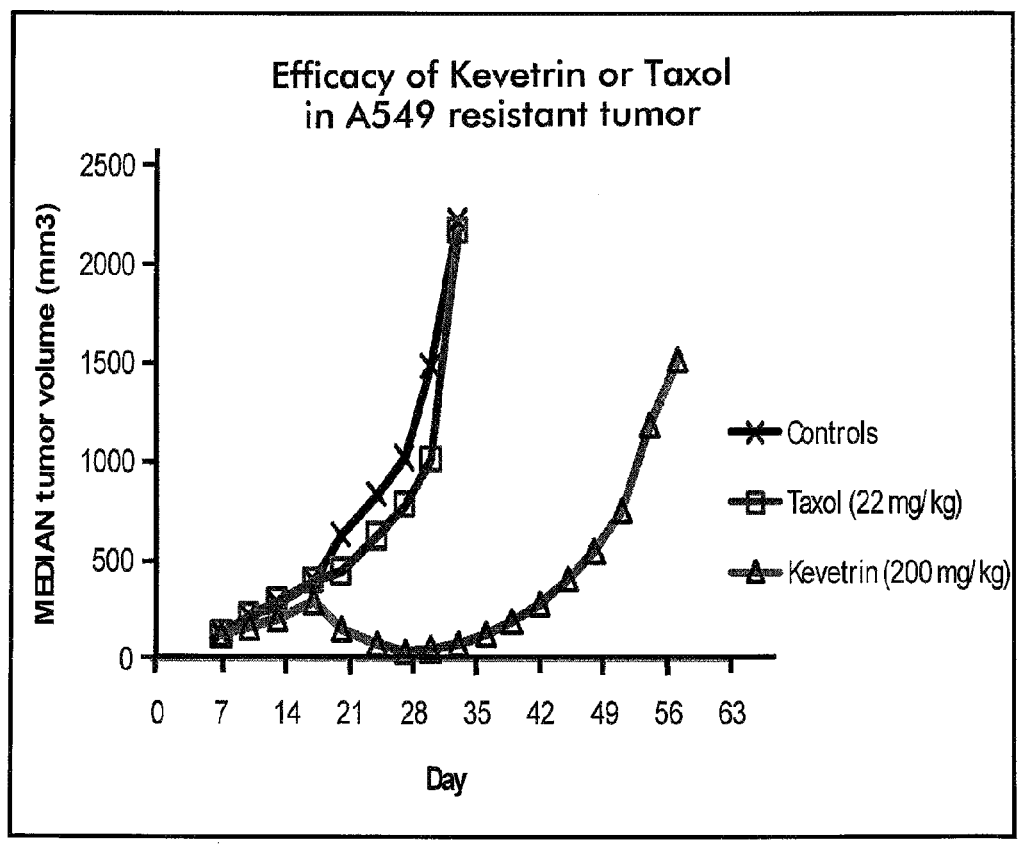
FIG. 8 shows efficacy of Kevetrin 200 mg/kg on days 7, 9 and 11 and against Taxol at 22 mg/kg on days 7, 9, 11 and 13 in A549 multi-drug resistant human lung carcinoma.

The animals were implanted subcutaneously with multi-drug resistant human lung carcinoma and the compounds were injected IV as per the schedule. Taxol had no effect on such cancer, whereas Kevetrin administered animals showed potent efficacy in the animals. The tumor growth was delayed about 26 days more than the untreated controls. The results are depicted in FIG. 8.

Efficacy of Kevetrin 200 mg/kg Days 7, 9, & 11 Against Taxol at 22 mg/kg on Days 7, 9, 11 & 13 in NCI-H1975 Multi-Drug Resistant Human Lung Carcinoma.

Figure 9:
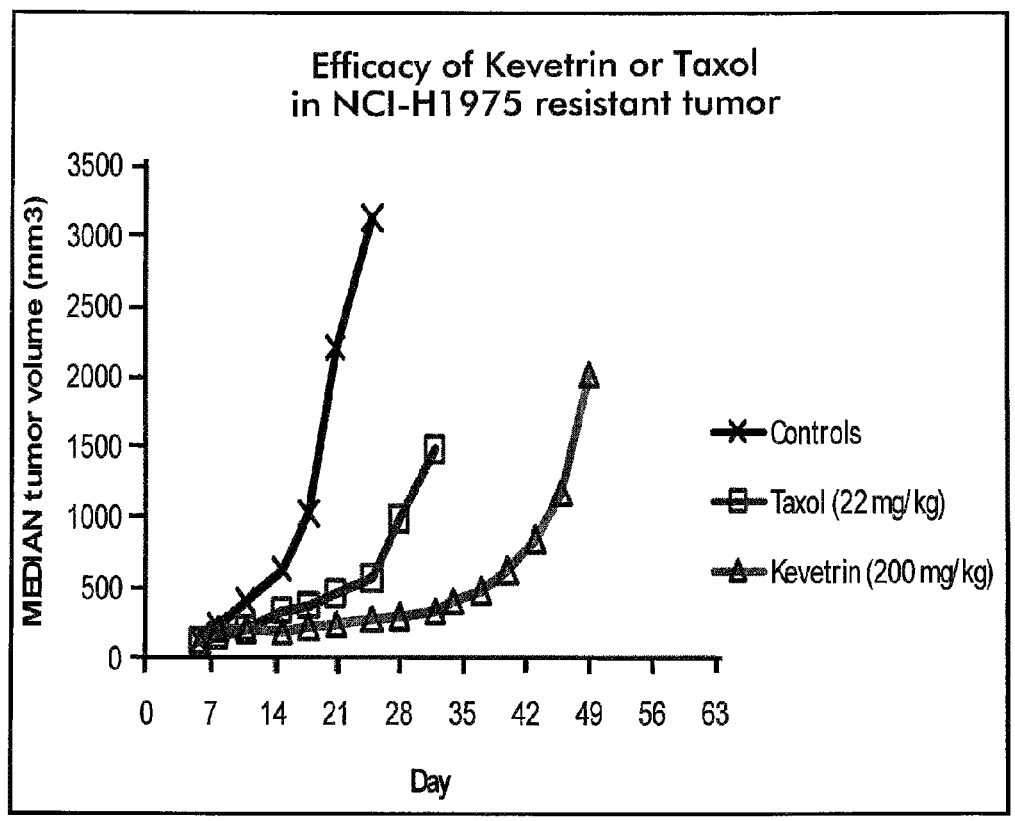
FIG. 9 shows efficacy of Kevetrin 200 mg/kg on days 7, 9 and 11 and against Taxol at 22 mg/kg on days 7, 9, 11 and 13 in NCI-H1975 multi-drug resistant human lung carcinoma.

The animals were implanted subcutaneously with another multi-drug resistant human lung carcinoma and the compounds were injected IV as per the schedule. Taxol had a limited effect on such cancer, whereas Kevetrin administered animals showed potent efficacy in the animals. The tumor growth was delayed about 9 days for Taxol treated animals and about 24 days more than the untreated controls. The results are depicted in FIG. 9.

All publications, including but not limited to books and journal articles, cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:

1. A method of treating a hyperproliferative disease selected from resistant non-small cell lung cancer, breast cancer, colon cancer, squamous cell carcinoma cancer, prostate cancer, head and neck cancer and glioma which comprises administering to a subject in need thereof a therapeutically effective amount of a compound of formula I or a pharmaceutically acceptable salt thereof

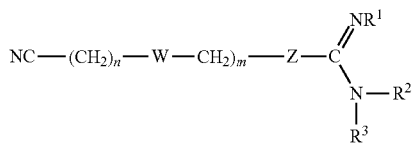

wherein, Z is selected from sulfur, copper, silver, gold and platinum, or Z is a halogen-containing moiety selected from $ClO_2$, $BrO_2$, and $IO_2$;

wherein n is zero or an integer from 1 to 8 and m is zero or an integer from 1 to 8;

$R^1$, $R^2$ and $R^3$ are independently selected from hydrogen, —$CH_2$-cyclohexyl, $C_1$-$C_6$ alkyl, $C_2$-$C_6$ alkenyl, and $C_2$-$C_6$ alkynyl, wherein the alkyl moieties of said alkyl, alkenyl and alkynyl groups may be linear, branched and cyclic and combinations of linear, branched and cyclic alkyl, alkenyl and alkynyl moieties and said groups may be substituted with groups selected from methyl, ethyl, propyl, isopropyl, n-butyl, t-butyl, methoxy, ethoxy, O-n-propyl, O-isopropyl, O-n-butyl, and O-t-butyl; or $R^1$ and $R^2$, taken together with the nitrogens to which they are directly attached and the carbon which is attached to the nitrogens, form a five or more membered ring, wherein p is an integer from 1 to 7 as shown below

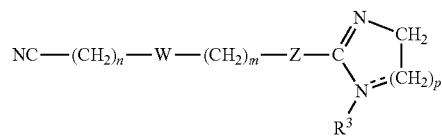

wherein the broken line represents an optional double bond, with the proviso that when there is such a double bond, $R^3$ is absent and the $CH_2$ group adjacent to the double bond has one hydrogen rather than two hydrogens, or $R^2$ and $R^3$ taken together with the nitrogen to which they are attached form a three or more membered ring, wherein p is an integer from 1 to 7, as shown below

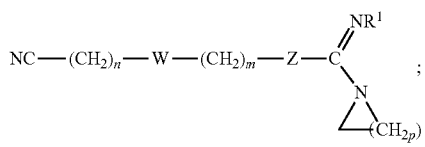

W is absent or W is selected from
—$CH_2$—, —$CH_2$—$CH_2$—, trans —CH=CH—, cis —CH=CH—, —C≡C—, or —$CHR^4$—$CHR^5$—, trans —C $R^4$=C $R^5$—, cis —$CR^4$=$CR^5$—, wherein $R^4$, and $R^5$ are independently selected from —$CH_2$-cyclohexyl, $C_1$-$C_6$ alkyl, $C_2$-$C_6$ alkenyl, $C_2$-$C_6$ alkynyl, and $C_1$-$C_6$ alkyl ether (also referred to as $C_1$-$C_6$ alkyl-O—); or W is a disubstituted moiety, wherein the term disubstituted is used to indicate how W is attached to the groups $(CH_2)_m$, and $(CH_2)_n$, selected from the group of disubstituted moieties consisting of (a) a 1,2-, 1,3-, or 1,4-disubstituted six membered ring which may be saturated or unsaturated with one, two or three double bonds; a 1,2-, or 1,3-disubstituted five membered ring which may be saturated or unsaturated with one or two double bonds; a 1,2-, or 1,3-disubstituted four membered ring which may be saturated or unsaturated with one or two double bonds; or a 1,2-disubstituted three membered ring which may be saturated and unsaturated with a double bond as shown by the following formulas, wherein the substituents on said disubstituted rings are the groups attached to W in formula I

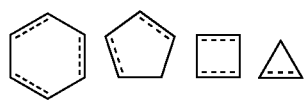

wherein the broken lines indicate optional double bonds;

(b) a 1,2-, 1,3-, or 1,4-disubstituted six membered ring which may be saturated or unsaturated with one, two or three double bonds; a 1,2-, or 1,3-disubstituted five membered ring which may be saturated or unsaturated with one or two double bonds; a 1,2-, or 1,3-disubstituted four membered ring which may be saturated or unsaturated with one or two double bonds; or a 1,2-disubstituted three membered ring which may be saturated and unsaturated with a double bond as shown by the following formulas, wherein the substituents on said disubstituted rings are the groups attached to W in formula I, and said disubstituted rings may have additional substituents $R^6$, $R^7$, $R^8$, and $R^9$ as shown in the following formulas

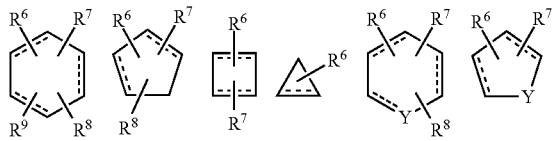

wherein the broken lines indicate optional double bonds; wherein $R^6$, $R^7$, $R^8$ and $R^9$ are independently selected from hydrogen, —$CH_2$-cyclohexyl, $C_1$-$C_6$ alkyl, $C_2$-$C_6$ alkenyl, $C_2$-$C_6$ alkynyl, or $C_1$-$C_6$ alkyl ether; the six membered ring may be saturated or have one, two or three double bonds, the five and four membered rings may be saturated or have one or two double bonds and the three membered ring may be saturated or have one double bond; wherein Y is nitrogen, oxygen, or sulphur;

(c) a ring selected from 1,2-, 1,3-, 1,4-, 1,5-, 1,6-, or 1,7- disubstituted saturated and unsaturated 9-membered rings with one or more double bonds, with ring positions numbered as shown in the first ring set forth below, said ring selected from the second to the thirteenth rings set forth below, wherein the substituents on said disubstituted rings are the groups attached to W in formula I, and said disubstituted rings may have additional substituents $R^6$, $R^7$, $R^8$, $R^9$ and $R^{10}$ as shown in the following formulas

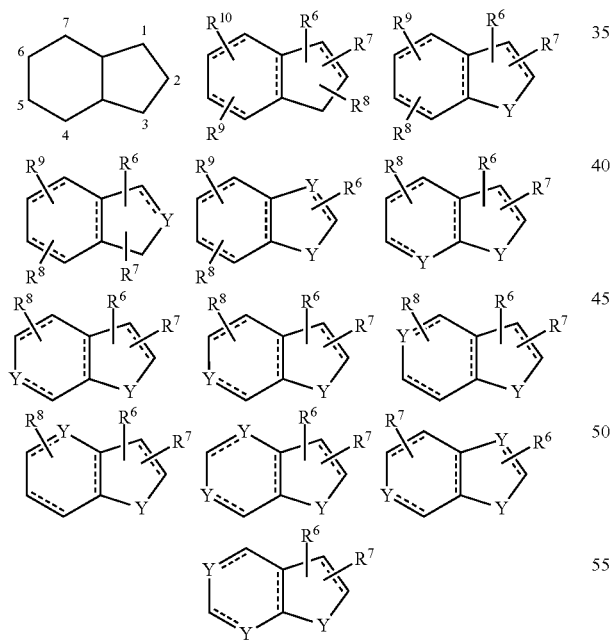

wherein the broken lines indicate optional double bonds; wherein $R^6$, $R^7$, $R^8$, $R^9$, and $R^{10}$ are independently selected from hydrogen, —$CH_2$-cyclohexyl, $C_1$-$C_6$ alkyl, $C_2$-$C_6$ alkenyl, $C_2$-$C_6$ alkynyl, or $C_1$-$C_6$ alkyl ether; wherein Y is nitrogen, oxygen, or sulfur;

(d) a ring selected from 1,2-, 1,3-, 1,4-, 1,5-, 1,6-, 1,7-, or 1,8- disubstituted saturated and unsaturated naphthalene rings with one or more double bonds, with ring positions numbered as shown in the first ring set forth below, said rings selected from the second to sixth rings set forth below, wherein the substituents on said disubstituted rings are the groups attached to W in formula I, and said disubstituted rings may have additional substituents $R^6$, $R^7$, $R^8$, $R^9$, $R^{10}$ and $R^{11}$ as shown in the following formulas

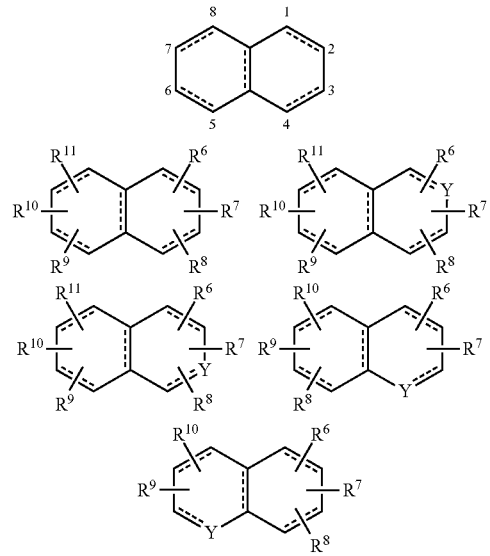

wherein the broken lines indicate optional double bonds; wherein $R^6$, $R^7$, $R^8$, $R^9$, $R^{10}$ and $R^{11}$ are independently selected from hydrogen, —$CH_2$-cyclohexyl, $C_1$-$C_6$ alkyl, $C_2$-$C_6$ alkenyl, $C_2$-$C_6$ alkynyl, or $C_1$-$C_6$ alkyl ether; wherein Y is nitrogen, oxygen, or sulphur; and (e) a ring selected from 1,2-, 1,3-, 1,4-, 1,5-, 1,6-, 1,7-,1,8-, 1,9-, 1,10-, 2,5-, 3,5-, 4,5-, or 5,10- disubstituted saturated and unsaturated anthracene rings with one or more double bonds, with ring positions numbered as shown in the first ring set forth below, said ring selected from the second to ninth rings set forth below, wherein the substituents on said disubstituted rings are the groups attached to W in formula I, and said disubstituted rings may have additional substituents $R^6$, $R^7$, $R^8$, $R^9$, $R^{10}$, $R^{11}$, $R^{12}$ and $R^{13}$ as shown in the following formulas

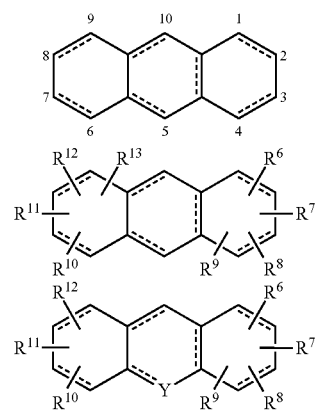

-continued

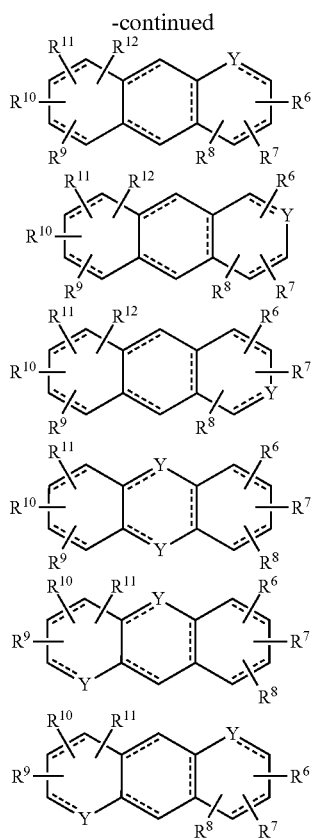

wherein the broken lines indicate optional double bonds; wherein $R^6$, $R^7$, $R^8$, $R^9$, $R^{10}$, $R^{11}$, $R^{12}$, and $R^{13}$ are independently selected from hydrogen, —CH$_2$-cyclohexyl, $C_1$-$C_6$ alkyl, $C_2$-$C_6$ alkenyl, $C_2$-$C_6$ alkynyl, or $C_1$-$C_6$ alkyl ether; wherein Y is nitrogen, oxygen, or sulfur.

2. A method according to claim 1 wherein said compound is a compound of formula I

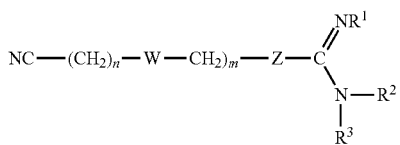

wherein, W is absent, Z is sulphur, n is zero or an integer from 1 to 8 and m is zero or an integer from 1 to 8;

R1, R2 and R3 are independently selected from hydrogen, CH2-cyclohexyl, C1-6 alkyl, C2-C6 alkenyl, and C2-C6 alkynyl, wherein the alkyl moieties of said alkyl, alkenyl and alkynyl groups may be linear, branched and cyclic and combinations of linear, branched and cyclic alkyl, alkenyl and alkynyl moieties and said groups may be substituted with groups selected from methyl, ethyl, propyl, isopropyl, n-butyl, t-butyl, methoxy, ethoxy, O-n-propyl, O-isopropyl, O-n-butyl, and O-t-butyl; or R1 and R2, taken together with the nitrogens to which they are directly attached and the carbon which is attached to the nitrogens, form a five or more membered ring, wherein p is an integer from 1 to 7 as shown below

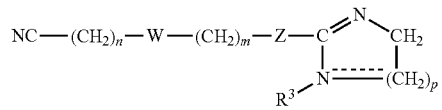

wherein the broken line represents an optional double bond, with the proviso that when there is such a double bond, R3 is absent and the CH2 group adjacent to the double bond has one hydrogen rather than two hydrogens, or R2 and R3 taken together with the nitrogen to which they are attached form a three or more membered ring, wherein p is an integer from 1 to 7, as shown below

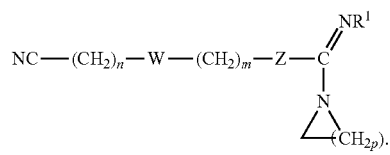

3. A method according to claim 2 wherein said hyperproliferative disease is resistant non-small cell lung cancer.

4. A method according to claim 2 wherein said hyperproliferative disease is breast cancer.

5. A method according to claim 2 wherein said hyperproliferative disease is colon cancer.

6. A method according to claim 2 wherein said hyperproliferative disease is squamous cell carcinoma cancer.

7. A method according to claim 2 wherein said hyperproliferative disease is prostate cancer.

8. A method according to claim 2 wherein said hyperproliferative disease is head or neck cancer.

9. A method according to claim 2 wherein said hyperproliferative disease is glioma.

* * * * *